US008626287B2

(12) United States Patent
Hareland

(10) Patent No.: US 8,626,287 B2
(45) Date of Patent: Jan. 7, 2014

(54) SHORT CIRCUIT FAULT-TOLERANCE IN AN IMPLANTABLE MEDICAL DEVICE

(75) Inventor: Scott A. Hareland, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/221,617

(22) Filed: Aug. 30, 2011

(65) Prior Publication Data

US 2013/0053911 A1 Feb. 28, 2013

(51) Int. Cl.
*A61N 1/39* (2006.01)

(52) U.S. Cl.
USPC .............................................................. 607/7

(58) Field of Classification Search
USPC ........................................ 607/7, 8, 27, 28, 5
See application file for complete search history.

(56) References Cited

U.S. PATENT DOCUMENTS

| | | | | |
|---|---|---|---|---|
| 5,344,430 | A * | 9/1994 | Berg et al. | 607/8 |
| 5,873,893 | A * | 2/1999 | Sullivan et al. | 607/5 |
| 6,493,586 | B1 * | 12/2002 | Stahmann et al. | 607/27 |
| 7,764,998 | B1 * | 7/2010 | Raddatz | 607/5 |
| 2008/0300660 | A1 | 12/2008 | John | |
| 2008/0306561 | A1 | 12/2008 | Sweeney | |
| 2010/0228307 | A1 | 9/2010 | Kroll et al. | |

OTHER PUBLICATIONS

Office Action from U.S. Appl. No. 13/221,558 dated Oct. 19, 2012 (6 pages).
U.S. Appl. No. 13/221,558, by Scott A. Hareland, filed Aug. 30, 2011.
Response from related U.S. Appl. No. 13/221,558, filed Jan. 22, 2013 (6 pages).

* cited by examiner

*Primary Examiner* — George Evanisko
(74) *Attorney, Agent, or Firm* — Michael C. Soldner

(57) ABSTRACT

A device includes an energy storage device, a plurality of electrodes, a memory, a switching circuit, and a processing module. The energy storage device stores electrical energy for delivery of defibrillation therapy to a heart. The memory stores N therapy configurations that define which of the plurality of electrodes are used to deliver defibrillation therapy and a waveform to be applied during delivery of defibrillation therapy. The switching circuit connects the plurality of electrodes to the energy storage device. The processing module controls the switching circuit to deliver defibrillation therapy according to a first therapy configuration of the N therapy configurations, detects a short circuit fault during delivery of the defibrillation therapy according to the first therapy configuration, and selects a second therapy configuration of the N therapy configurations based on when the short circuit fault was detected during delivery of the defibrillation therapy according to the first therapy configuration.

14 Claims, 21 Drawing Sheets

Reconfiguration Options for Short Circuit Faults

| Delivery Attempted | Status (PW1/PW2) | Possible Cause | Next Vector |
|---|---|---|---|
| AX>B biphasic | OK/OK | none | as programmed |
| AX>B biphasic | OK/short | $A_H$, $X_H$, or $B_L$ short | AX>B monophasic |
| AX>B biphasic | short/na | HVX→HVB short<br>HVB→HVA short<br>$A_L$, $X_L$, or $B_H$ short | A>B biphasic |
| A>B biphasic | OK/OK | none if this is a non-HVX system<br>–OR–<br>HVX→HVB short | A>B |
| A>B biphasic | OK/short | $A_H$ or $B_L$ short | AX>B monophasic |
| A>B biphasic | short/na | HVB→HVA short<br>$A_L$ or $B_H$ short | B>X biphasic<br>- followed by -<br>B>A monophasic if B>X biphasic is electrically OK (no shorts) but not effective as a therapy |
| B>X biphasic | OK/OK | HVB→HVA short | B>X biphasic |
| B>X biphasic | short/na | $X_L$ or $B_H$ short | B>AX monophasic |
| B>X biphasic | OK/short | $X_H$ or $B_L$ short | AX>B monophasic |

FIG. 21

SHORT CIRCUIT FAULT-TOLERANCE IN AN IMPLANTABLE MEDICAL DEVICE

TECHNICAL FIELD

The disclosure relates to techniques for providing fault tolerance in an implantable medical device, and more particularly, to techniques for providing tolerance to short circuit faults in an implantable medical device.

BACKGROUND

Implantable medical devices (IMDs), such as implantable cardioverter-defibrillators, may detect a cardiac arrhythmia and provide various electrical therapies in response to detection of the arrhythmia. Therapies provided by an IMD in response to a detected arrhythmia may include anti-tachycardia pacing (ATP) therapy, cardioversion therapy, and/or defibrillation therapy, depending on the type of arrhythmia detected.

Some detected arrhythmias may be life-threatening. Ventricular tachycardia (VT) and ventricular fibrillation (VF) may be considered to be life-threatening arrhythmias. In examples where an IMD detects such a life-threatening arrhythmia, the IMD may provide a defibrillation shock to the patient's heart in order to correct the arrhythmia and return the patient's heart rhythm back to a normal rhythm.

An IMD may include components that are dedicated to producing a defibrillation shock in response to detection of a life-threatening arrhythmia. For example, an IMD may include high-voltage capacitors for storing electrical charge for subsequent delivery during a defibrillation shock. Additionally, the IMD may include a delivery circuit that transfers the electrical charge from the high-voltage capacitors to the heart. During operation, an IMD may typically monitor a patient's heart rate, or other parameters (e.g., morphology, onset, etc.) in order to detect an arrhythmia. If the IMD detects a life-threatening arrhythmia, the IMD may charge the high-voltage capacitors and control the delivery circuit to transfer the energy from the high-voltage capacitors to the patient's heart using either a biphasic or a monophasic waveform. Delivery of the defibrillation shock may terminate the detected arrhythmia and return the heart to a normal rhythm.

SUMMARY

An IMD according to the present disclosure (e.g., an implantable cardioverter-defibrillator) may detect cardiac arrhythmias and apply high-energy therapy (e.g., cardioversion and/or defibrillation) to the heart in order to correct the detected arrhythmia. The IMD may deliver high-energy therapy according to a therapy configuration that specifies an electrode vector to be used during delivery of the therapy and that specifies the type of waveform (e.g., biphasic/monophasic/multiphasic) to be used during deliver of the therapy. The IMD may include an energy storage device (e.g., high-voltage capacitors) that delivers the high-energy therapy through an electrical pathway to the patient's heart according to a specified therapy configuration. In some examples, the electrical pathway may include electrical switches, electrical interconnects, high-voltage leads, and electrodes.

Typically, energy is delivered from the energy storage device to the heart. However, in some examples, the electrical pathway may include short circuit faults that redirect current (e.g., shunt current) away from the heart during delivery of high-energy therapy. Such faults may be referred to herein as "short circuit faults." In general, short circuit faults may occur between any two electrical conductors that are typically insulated from one another during high-energy therapy, but, due to a short circuit fault, have become electrically coupled, e.g., via contact with one another. Short circuit faults may occur in or between various components of the electrical pathway of the IMD. In some examples, short circuit faults may occur between two conductors in a lead, or between an electrode and a conductor in a lead, or between two electrodes. In other examples, short circuit faults may include portions of the electrical interconnects in the electrical pathway not including the conductors in the leads or the electrodes. In still other examples, short circuit faults may occur in the switches used to deliver high-energy therapy.

The IMD of the present disclosure may detect short circuit faults in the electrical pathway during delivery of the high-energy therapy according to a current therapy configuration. If the IMD detects a short circuit fault while delivering therapy according to a currently selected therapy configuration, the IMD may select a subsequent therapy configuration. The IMD may select the subsequent therapy configuration based on the electrode vector used while the fault was detected, the waveform used while the fault was detected, and based on when the fault occurred during the waveform (e.g., during a first or second phase of the biphasic waveform).

The IMD may use the subsequent therapy configuration to treat subsequently detected arrhythmias. If any future short circuit faults are detected during delivery of high-energy therapy according to the subsequently selected therapy configuration, the IMD may select a newer therapy configuration. The IMD may select the newer therapy configuration in a similar manner described above, e.g., based on the electrode vector used while the fault was detected, based on the waveform used while the fault was detected, based on when the fault occurred during delivery, and in some examples, based on prior knowledge of other failed therapy attempts.

The IMD of the present disclosure may continue to update therapy configurations in response to additional detections of short circuit faults during delivery of high-energy therapy. In this manner, the IMD of the present disclosure may step through a variety of different therapy configurations in order to bypass one or more detected short circuit faults. Stepping through a variety of different therapy configurations based on which therapy configurations include short circuit faults and based on when those short circuit faults occur may provide for robust delivery of high-energy therapy from the IMD in the event of a fault in the IMD that is presented as a short circuit that shunts current away from the heart.

In one example according to the present disclosure, a medical device comprises an energy storage device, a plurality of electrodes, a memory, a switching circuit, and a processing module. The energy storage device is configured to store electrical energy for delivery of defibrillation therapy to a heart. The memory stores N therapy configurations, each of the N therapy configurations defining which of the plurality of electrodes are used to deliver defibrillation therapy and further defining a waveform to be applied during delivery of defibrillation therapy. N is an integer that is greater than 1. The switching circuit is configured to connect the plurality of electrodes to the energy storage device. The processing module is configured to control the switching circuit to deliver defibrillation therapy according to a first therapy configuration of the N therapy configurations and detect a short circuit fault during delivery of the defibrillation therapy according to the first therapy configuration. The processing module is further configured to select a second therapy configuration of the N therapy configurations based on when the short circuit fault was detected during delivery of the defibrillation therapy according to the first therapy configuration.

In another example according to the present disclosure, a medical device comprises an energy storage device, a plurality of electrodes, a switching circuit, and a processing module. The energy storage device is configured to store electrical energy for delivery of defibrillation therapy to a heart. The switching circuit is configured to connect the plurality of electrodes to the energy storage device. The processing module is configured to control the switching circuit to deliver defibrillation therapy using a first set of the plurality of electrodes and using a biphasic waveform that includes first and second phases. The processing module is further configured to detect a short circuit fault during one of the first and second phases of the biphasic waveform and select a second set of the plurality of electrodes and one of a biphasic or monophasic waveform for delivery of a subsequent defibrillation therapy. The selection is based on which one of the first and second phases of the biphasic waveform included the detected short circuit fault.

In another example according to the present disclosure, a method comprises storing N therapy configurations in a memory of a medical device, each of the N therapy configurations defining which of a plurality of electrodes are used to deliver defibrillation therapy and further defining a waveform to be applied during delivery of defibrillation therapy. N is an integer that is greater than 1. The method further comprises controlling a switching circuit to deliver defibrillation therapy from an energy storage device according to a first therapy configuration of the N therapy configurations and detecting a short circuit fault during delivery of the defibrillation therapy according to the first therapy configuration. Additionally, the method comprises selecting a second therapy configuration of the N therapy configurations based on when the short circuit fault was detected during delivery of the defibrillation therapy according to the first therapy configuration.

The details of one or more examples are set forth in the accompanying drawings and the description below. Other features, objects, and advantages will be apparent from the description and drawings, and from the claims.

BRIEF DESCRIPTION OF THE DRAWINGS

FIG. 21 shows a table that describes possible causes of short circuit faults in the IMD and lists therapy reconfigurations that may be used to overcome the short circuit faults.

DETAILED DESCRIPTION

Figure 1:
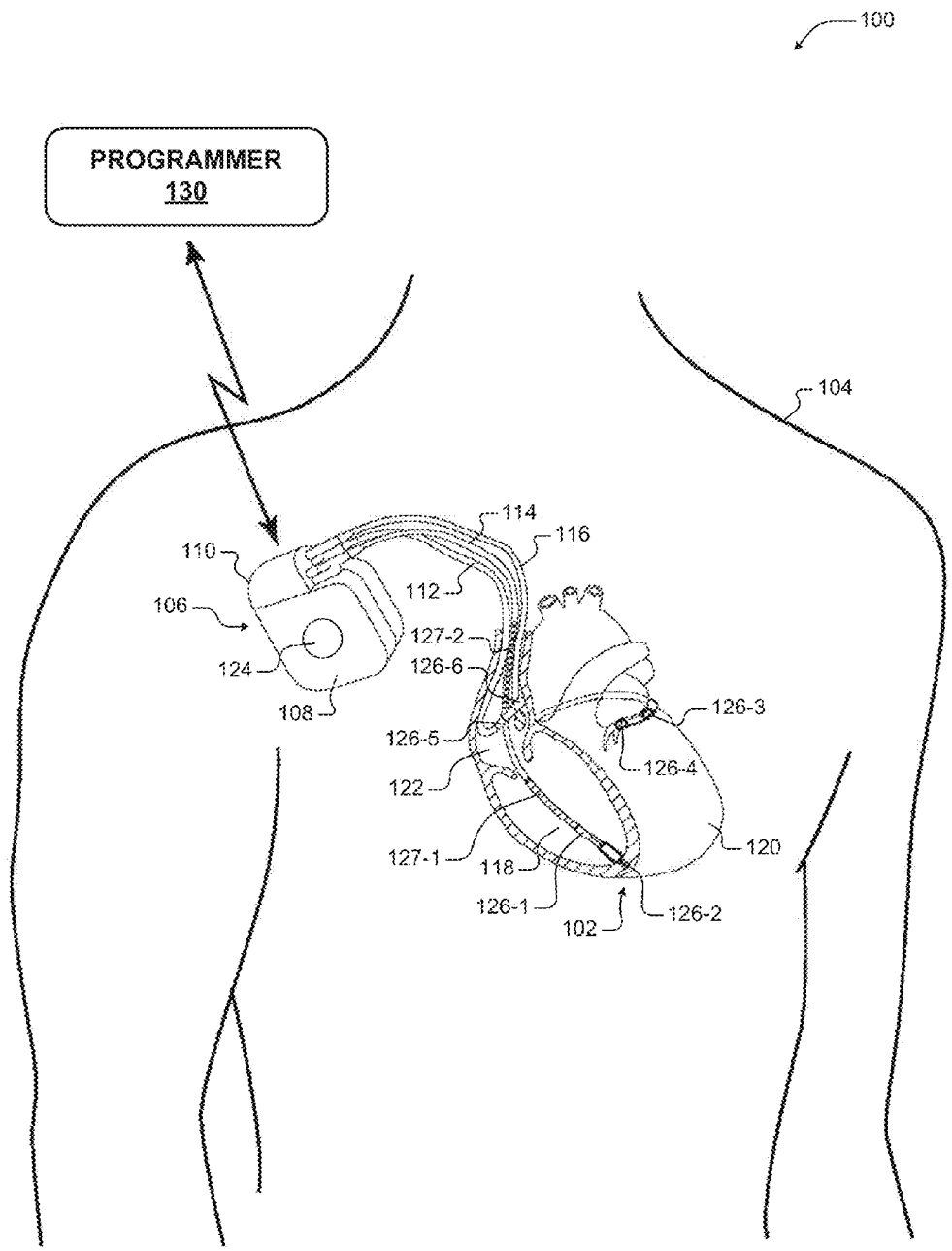
FIG. 1 shows an example system including an implantable medical device (IMD) that may be used to diagnose conditions of and provide therapy to a heart of a patient.

An IMD according to the present disclosure may detect an arrhythmia (e.g., VT/VF) and deliver therapy to terminate the arrhythmia. In some examples, the IMD may deliver defibrillation therapy in response to detection of potentially life-threatening arrhythmias, such as VT/VF. In other examples, the IMD may deliver cardioversion therapy in response to the detection of potentially life threatening arrhythmias. High-energy electrical therapies, such as defibrillation therapy and cardioversion therapy, delivered by the IMD in response to detection of potentially life-threatening arrhythmias may be referred to hereinafter as "high-energy therapies." Arrhythmias that may be typically treated by such high-energy therapies, such as VF/VT, may be referred to hereinafter as "shockable arrhythmias."

The IMD of the present disclosure may include an energy storage device (e.g., high-voltage capacitors) that may be used to store charge used during delivery of high-energy therapy. The IMD may monitor the heart rhythm of the patient and, in response to detection of a shockable arrhythmia, store charge on the energy storage device and subsequently deliver the high-energy therapy to the patient using the stored charge. The IMD may deliver the high-energy therapy using a variety of electrical waveforms and electrode combinations. For example, the IMD may delivery the high-energy therapy using either a monophasic or biphasic waveform. Although high-energy therapy is described herein as being delivered using either a monophasic or biphasic waveform, it is contemplated that high-energy therapy may be delivered using other waveforms, such as multiphasic waveforms.

The IMD may deliver the high-energy therapy to the heart using a plurality of different electrode combinations. In some examples, the IMD may deliver high-energy therapy using three electrodes, while in other examples, the IMD may deliver high-energy therapy using two electrodes. The combination of electrodes used to deliver the high-energy therapy may referred to hereinafter as an "electrode vector." As described herein, high-energy therapy may be delivered using the following electrodes: 1) electrode HVA, which is an electrode on the housing (i.e., can) of the IMD, 2) electrode HVB, which may be a defibrillation coil electrode in the right ventricle, and 3) electrode HVX, which may be a defibrillation coil electrode in the superior vena cava. An electrode vector may include any combination of the electrodes HVA, HVB, and HVX. Although electrodes HVA, HVB, and HVX are described herein as delivering high-energy therapy, it is contemplated that the IMD may deliver therapy using other electrodes. For example, the IMD may delivery therapy using a greater number of electrodes, or in some cases, other types of electrodes, such as patch electrodes.

Electrode vectors may be described using a notation that includes the greater-than symbol ">" to indicate the direction of current between electrodes during delivery of high-energy therapy. In one example, electrode vector "AX>B" may indicate that the direction of current is from the HVA electrode and HVX electrode to the HVB electrode. Example electrode vectors described herein that include three electrodes are electrode vectors "AX>B" and "B>AX." Electrode vectors described herein that include only two electrodes are electrode vectors "A>B", "B>A", "X>B", and "B>X." In some examples, electrode vectors may also include "A>X" and "X>A." While vectors "A>X" and "X>A" may not be conventionally used vectors, in some examples, "A>X" and "X>A" may provide a valid path, e.g., in the case where an epicardial patch electrode is connected as "X."

The IMD may include a memory that stores various high-energy therapy configurations. Each high-energy therapy configuration may specify an electrode vector and an electrical waveform to be delivered by the electrode vector. High-energy therapy configurations may be referred to hereinafter as "therapy configurations." One example therapy configuration may specify that high-energy therapy is to be delivered via electrode vector AX>B using a biphasic waveform. In other examples, therapy configurations may specify that high-energy therapy is to be delivered via electrode vector AX>B using a monophasic waveform, via electrode vector B>AX using a monophasic waveform, or via electrode vector B>AX using a biphasic waveform. In other examples, therapy configurations may specify that high-energy therapy is to be delivered via electrode vector A>B using a biphasic waveform, via electrode vector A>B using a monophasic waveform, via electrode vector B>A using a biphasic waveform, or via electrode vector B>A using a monophasic waveform. In still other examples, therapy configurations may specify that high-energy therapy is to be delivered via electrode vector X>B using a biphasic waveform, via electrode vector X>B using a monophasic waveform, via electrode vector B>X using a biphasic waveform, or via electrode vector B>X using a monophasic waveform. In some examples, the therapy configurations may also specify an amount of energy to be delivered.

The IMD of the present disclosure includes a processing module that detects shockable arrhythmias, controls charging of the energy storage device in response to detection of a shockable arrhythmia, and controls delivery of high-energy therapy according to a selected therapy configuration. The IMD may include a switching circuit that may be controlled in order to deliver the high-energy therapy according to the selected therapy configuration. Under control of the processing module, the switching circuit may connect the energy storage device to the electrode vector such that the waveform of the selected therapy configuration is delivered to the patient via the electrode vector of the selected therapy configuration.

The IMD of the present disclosure may detect a potential fault during delivery of the high-energy therapy. For example, the IMD may detect a short circuit fault during delivery of the high-energy therapy. A short circuit fault may generally describe a variety of different faults that may occur in the conductive pathways leading from the energy storage device to the electrodes during delivery of high-energy therapy. Generally, a short circuit fault may refer to an electrical fault in the IMD that may redirect (e.g., shunt) current delivered by the energy storage device such that the redirected current is not delivered to the heart. In other words, short circuit faults may divert current delivered by the energy storage device away from a path through the heart. When a short circuit fault is not present in the conductive pathway between the energy storage device and the heart, the conductive pathway delivers substantially all of the current from the energy storage device to the patient. The presence of a short circuit fault, however, may cause a substantial portion of current delivered from the energy storage device to be redirected (e.g., shunted) along a different electrical path, rather than being delivered to the patient. The impedance of a short circuit fault may vary. In some examples, the short circuit fault may be a complete short (i.e., near zero resistance), while in other examples, the short circuit fault may not be a complete short but may still present a low enough impedance to shunt current away from the heart and disrupt the delivery of therapy.

Short circuit faults may include a variety of different faults within the IMD. A short circuit fault may generally occur between any two conductive components in the IMD that are included in the electrical path during delivery of high-energy therapy. Components of the IMD that may be included in a short circuit fault may include switches, interconnects, conductors in leads of the IMD, and electrodes at the end of the conductors. Each of these components, when functional, may form a portion of the delivery pathway that delivers current from the energy storage device to the heart. However, a short circuit fault within or between any of these components may cause current to be directed away from the heart, and instead dissipated in the components of the IMD.

In some examples, two conductors of a lead may short together such that current delivered from the energy storage device is shunted between the conductors and not delivered to the heart. The shorting of two conductors of a lead may occur at any point along the entire length of the lead from the point where the lead is attached to a connector block to a point where the electrodes of the lead are implanted in the heart. A short between two conductors of a lead may also occur within the connector block of the IMD. In some examples, short circuit faults may occur between an electrode and a conductor in a lead, or may occur between two electrodes. In some examples, short circuit faults may occur between portions of the electrical interconnects in the electrical pathway not including the conductors in the leads or the electrodes. Electrical interconnects may generally describe the conductive paths between electrical components within the IMD, and may include the conductive traces, e.g., on a printed-circuit board. In still other examples, short circuit faults may occur in the switches used to deliver high-energy therapy. For example, a switch including a short circuit fault may generally act as a low impedance path (e.g., a short circuit), even when the switch is instructed to open.

A short circuit fault in the conductive pathway may tend to shunt current through components of the IMD instead of delivering the current to the heart, which may tend to slow the rate at which energy is delivered to the heart during delivery of high-energy therapy. Although a short circuit fault may decrease the rate at which energy is delivered to the heart, energy may be drained from the energy storage device at a greater rate when a short circuit fault is present due to the low impedance path produced by the short circuit fault. The processing module of the IMD may monitor the delivery of energy to the patient, and may detect a potential short circuit fault when greater than a threshold amount of current is being delivered from the energy storage device during delivery of the high-energy therapy. The delivery of a large amount of current (e.g., greater than the threshold amount) from the energy storage device may indicate that the current is not being delivered to the heart, but instead, that the electrical pathway includes a low impedance path (e.g., a short circuit) that is redirecting the current and preventing delivery to the heart. In other words, when a short circuit fault is not present in the delivery pathway, the current delivered to the heart may encounter a relatively high impedance path at the heart that prevents higher currents (i.e., greater than the threshold amount) from being delivered from the energy storage device. The threshold amount of current may be a value selected such that an amount of current greater than the threshold amount may indicate that current is being delivered through a short circuit fault instead of the heart. The threshold amount may also be selected such that an amount of current that is less than the threshold amount may indicate that current is being delivered to the heart and not through a short circuit fault.

As described above, the IMD may deliver therapy according to a selected therapy configuration. Initially, the IMD may deliver therapy according to a set of initial therapy configurations stored in memory. The initial therapy configurations may define a pattern of selection of therapy configurations used by the IMD when a short circuit fault has not been previously detected during delivery of therapy. Accordingly, the processing module may control delivery of high-energy therapy according to the initial therapy configurations in response to detection of arrhythmia, assuming a short circuit fault has not been detected during prior deliveries of high-energy therapy according to the initial therapy configurations.

The initial therapy configurations stored in memory may define a pattern of selection of therapy configurations that may be used by the IMD during attempts to treat a detected shockable arrhythmia. For example, the IMD may initially attempt to treat a shockable arrhythmia using a first one of the initial therapy configurations. If successful in treating the shockable arrhythmia, the IMD may return to monitoring the patient's heart rhythm. If unsuccessful in treating the shockable arrhythmia, the IMD may select a second one of the initial therapy configurations to treat the shockable arrhythmia. In this manner, the IMD may select consecutive therapy configurations from the initial therapy configurations in order to attempt to treat a shockable arrhythmia in different ways until a successful treatment is found.

The initial therapy configurations may be programmed into the device prior to implantation, e.g., as factory default settings or programmed by a clinician. In other examples, the initial therapy configurations may be updated by a clinician, using a programmer, after the device is implanted. The initial therapy configurations may define a variety of different electrode vector and waveform combinations, as well as different amounts of energies to be delivered during high-energy therapy.

The IMD may deliver high-energy therapy according to the initial therapy configurations until a short circuit fault is detected during delivery of the high-energy therapy according to the initial therapy configurations. Upon detection of a short circuit fault during delivery of high-energy therapy according to the initial therapy configurations, the IMD may begin delivering high-energy therapy according to a set of short circuit therapy configurations stored in memory. The short circuit therapy configurations may define the selection of therapy configurations used by the IMD after a short circuit fault is detected during delivery of high-energy therapy. Accordingly, after detection of a short circuit fault, the processing module may control delivery of high-energy therapy according to the short circuit therapy configurations in response to detection of a shockable arrhythmia.

Each of the short circuit therapy configurations stored in memory may define an electrode vector (e.g., AX>B, A>X, etc.), a waveform (e.g., biphasic/monophasic), and transition data. The transition data may define a subsequent therapy configuration to select in response to detection of a short circuit fault at the current therapy configuration. For example, if the processing module detects a short circuit fault at a first therapy configuration, the processing module may determine a subsequent (i.e., second) therapy configuration to use by looking at the transition data that is associated with the current (i.e., first) therapy configuration. The processing module may then set the therapy configuration of the IMD to the second therapy configuration in order to attempt to bypass the potential fault. If a short circuit fault is then detected in the second therapy configuration, the processing module may set the therapy configuration to the therapy configuration indicated by the transition data of the second therapy configuration. In this manner, the IMD may determine a subsequent therapy configuration to use for the delivery of high-energy therapy based on the current therapy configuration in which a short circuit fault is detected.

In addition to determining subsequent therapy configurations based on a current therapy configuration in which a short circuit fault is detected, the IMD may also determine the subsequent therapy selection based when the short circuit fault was detected during the delivery of high-energy therapy. Accordingly, the IMD of the present disclosure may select a subsequent therapy configuration based on the current therapy configuration in which a fault is detected and based on when the detected fault occurred during delivery of high-energy therapy according to the current therapy configuration.

The transition data may specify the subsequent therapy configuration based on when the short circuit fault was detected during the current therapy configuration. For example, the transition data associated with a first therapy configuration may define a second therapy configuration if a short circuit fault is detected during the first phase of the biphasic waveform of the first therapy configuration, and the transition data associated with the first therapy configuration may define a third therapy configuration if a short circuit fault is detected during the second phase of the biphasic waveform of the first therapy configuration. In examples where the IMD may deliver a multiphasic waveform, transition data may specify a subsequent therapy based on which phase of the multiphasic waveform included a fault.

In summary, the IMD of the present disclosure may detect shockable arrhythmias and provide high-energy therapy according to a selected configuration therapy. If the IMD detects a short circuit fault during delivery of the high-energy therapy according to a currently selected therapy configuration, the IMD may select a subsequent therapy configuration based on the parameters of the current therapy configuration (e.g., the electrode vector and waveform) and based on when the short circuit fault occurred during delivery according to the current therapy configuration (e.g., during either the first or second phase of a biphasic waveform). In this manner, the IMD of the present disclosure may step through a variety of different therapy configurations in order to bypass one or more detected short circuit faults. Stepping through a variety of different therapy configurations based on which therapy configurations include short circuit faults and based on when those short circuit faults occur may provide for robust delivery of high-energy therapy from the IMD in the event of a fault in a conductive pathway of the IMD that is presented as a short circuit fault that shunts energy away from the heart.

Figure 2:
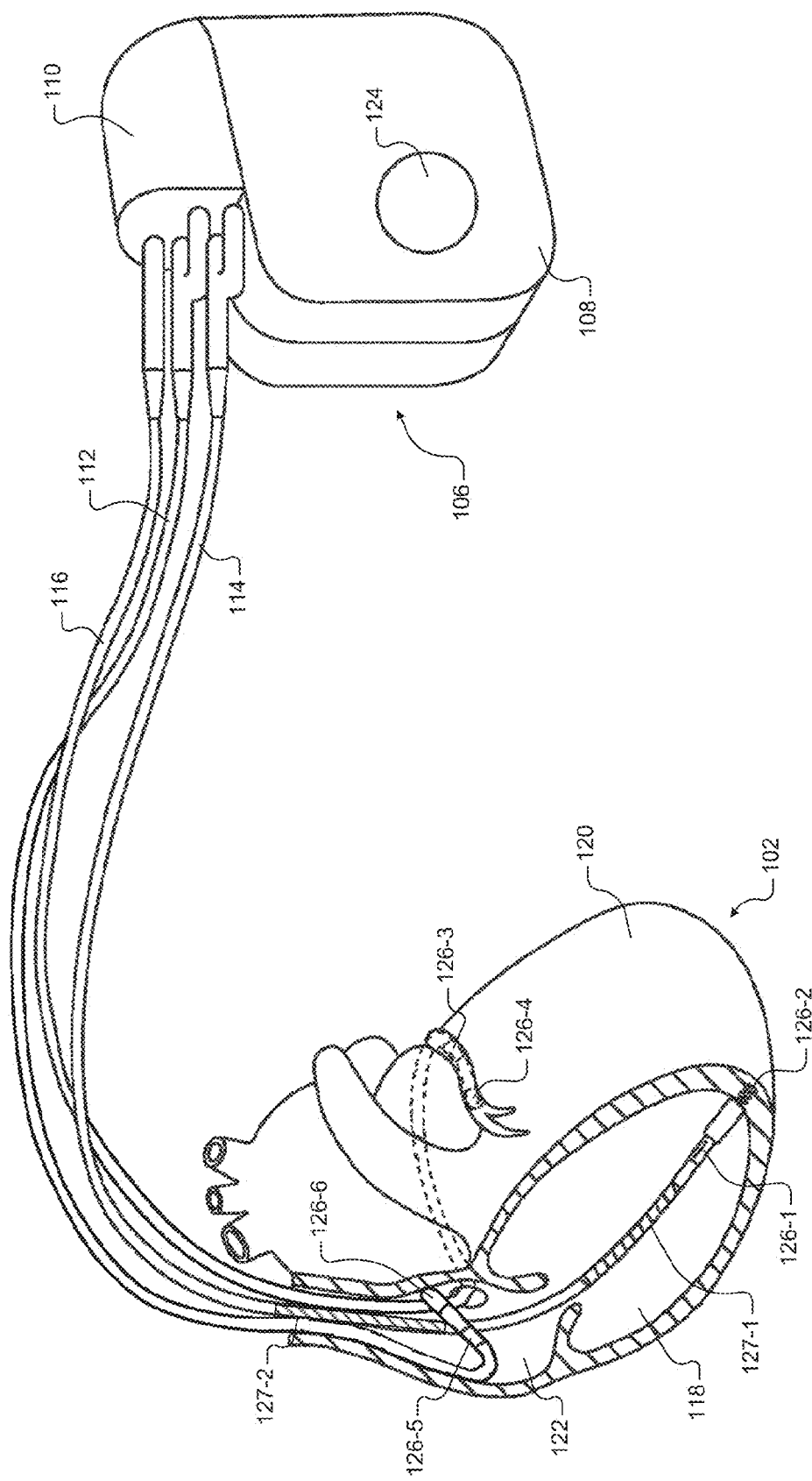
FIG. 2 shows a detailed view of the IMD of FIG. 1.
Figure 3:
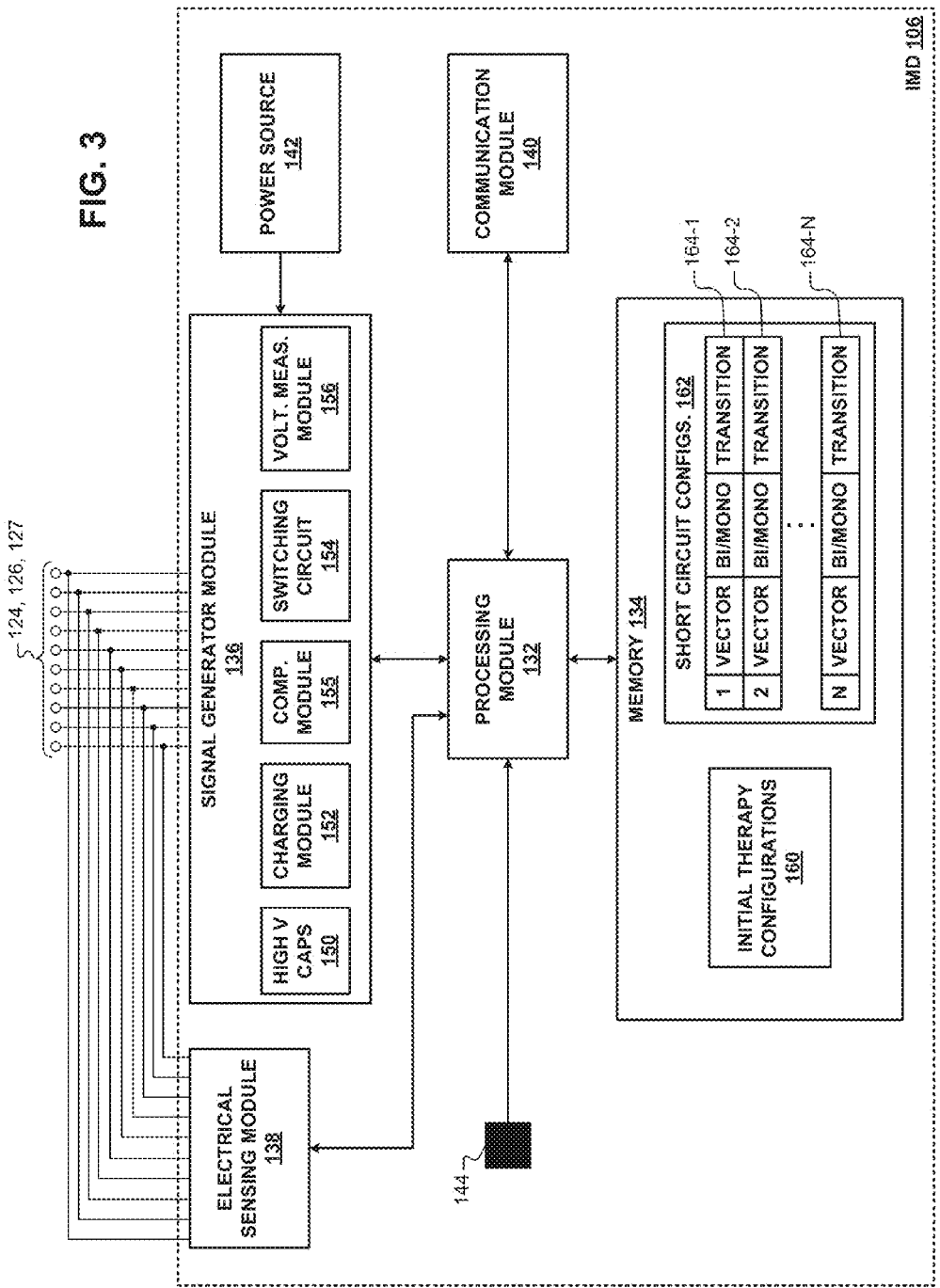
FIG. 3 shows a functional block diagram of an example IMD.
Figure 4:
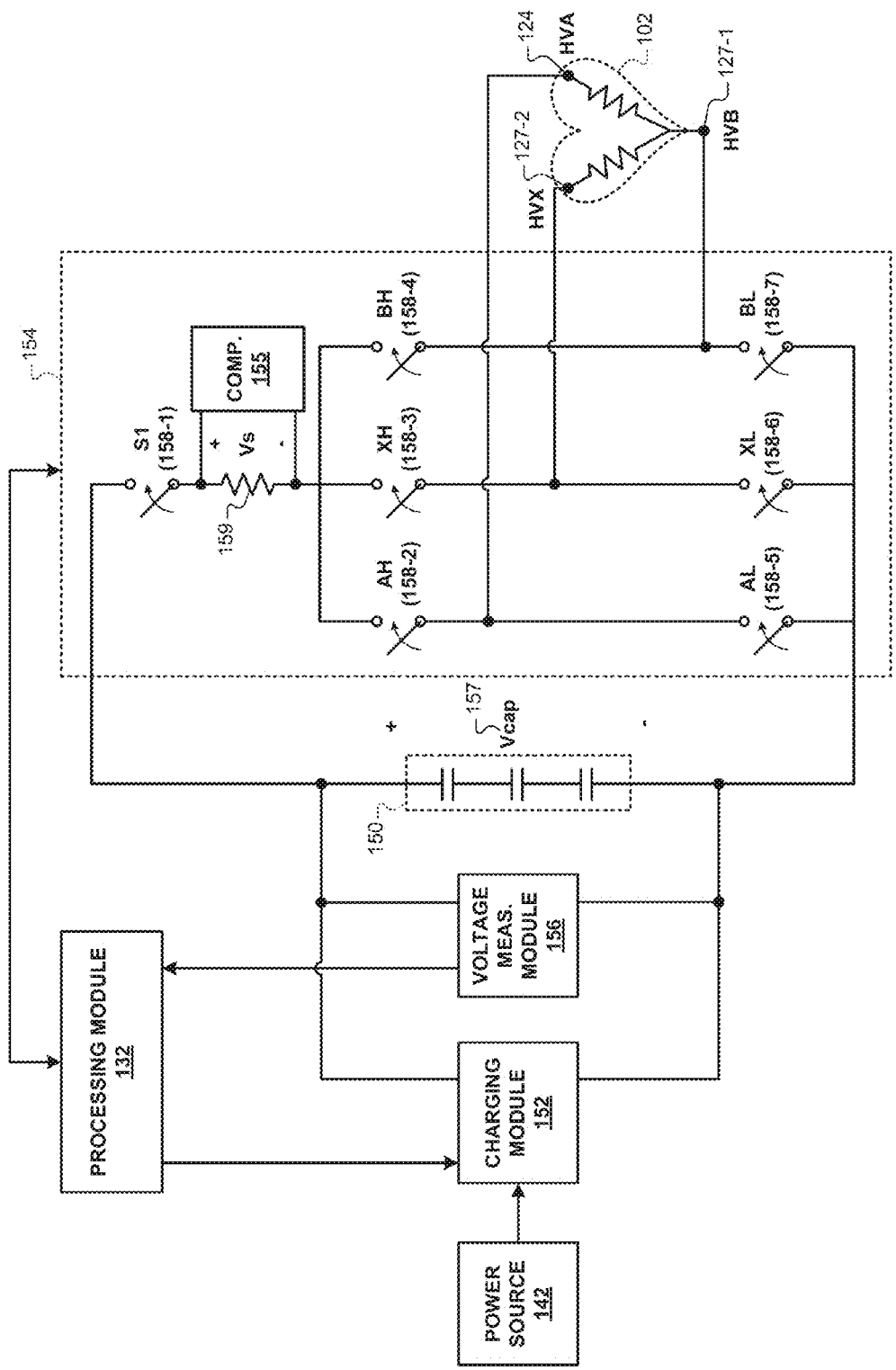
FIG. 4 shows example components of the IMD of FIG. 3 that control charging of high-voltage capacitors, deliver high-energy therapy to the heart of the patient, and monitor the amount of current being delivered during the high-energy therapy.
Figure 15:
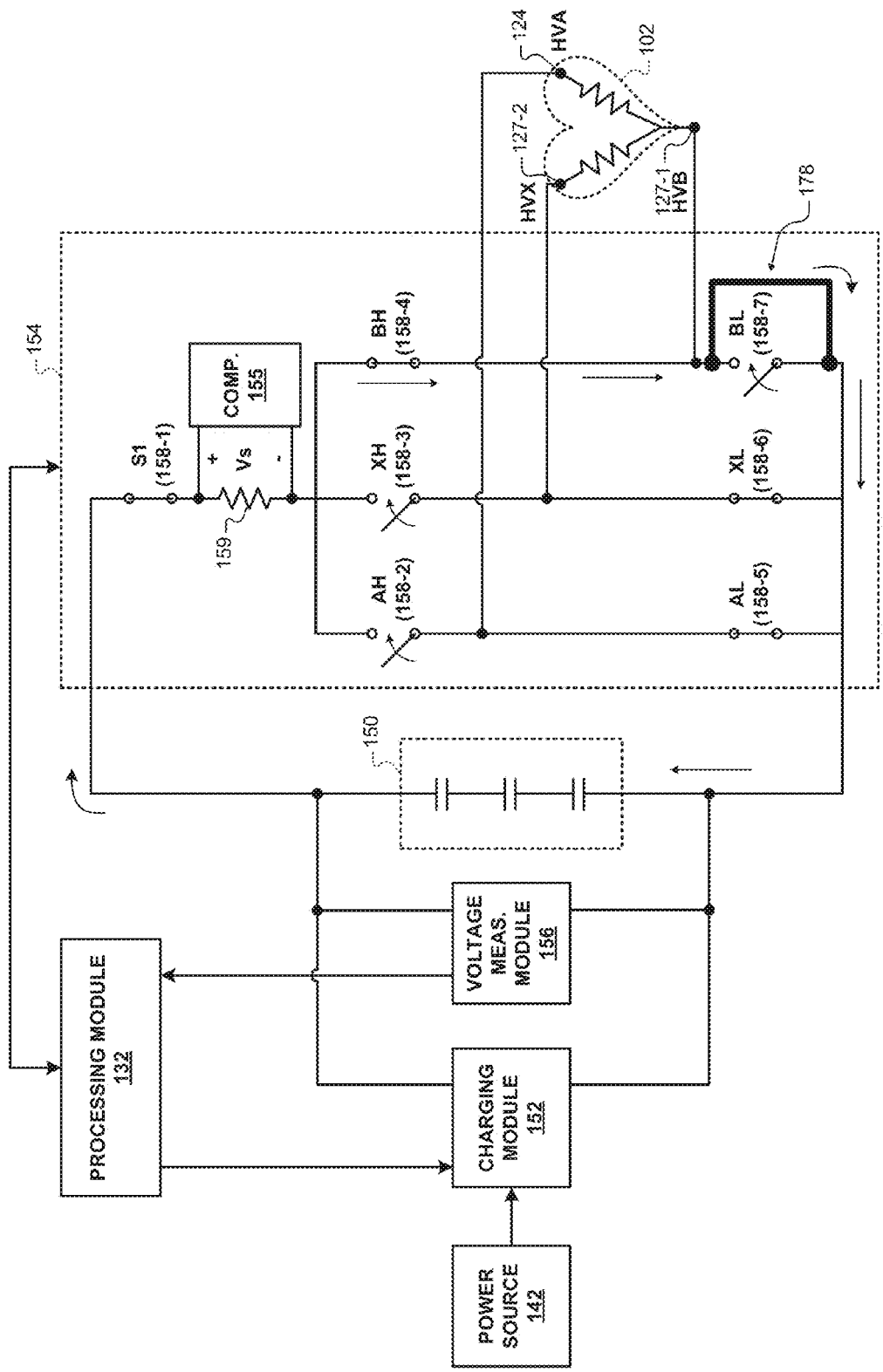
FIG. 15 is a schematic that illustrates another short circuit fault in a switch of the IMD.
Figure 16:
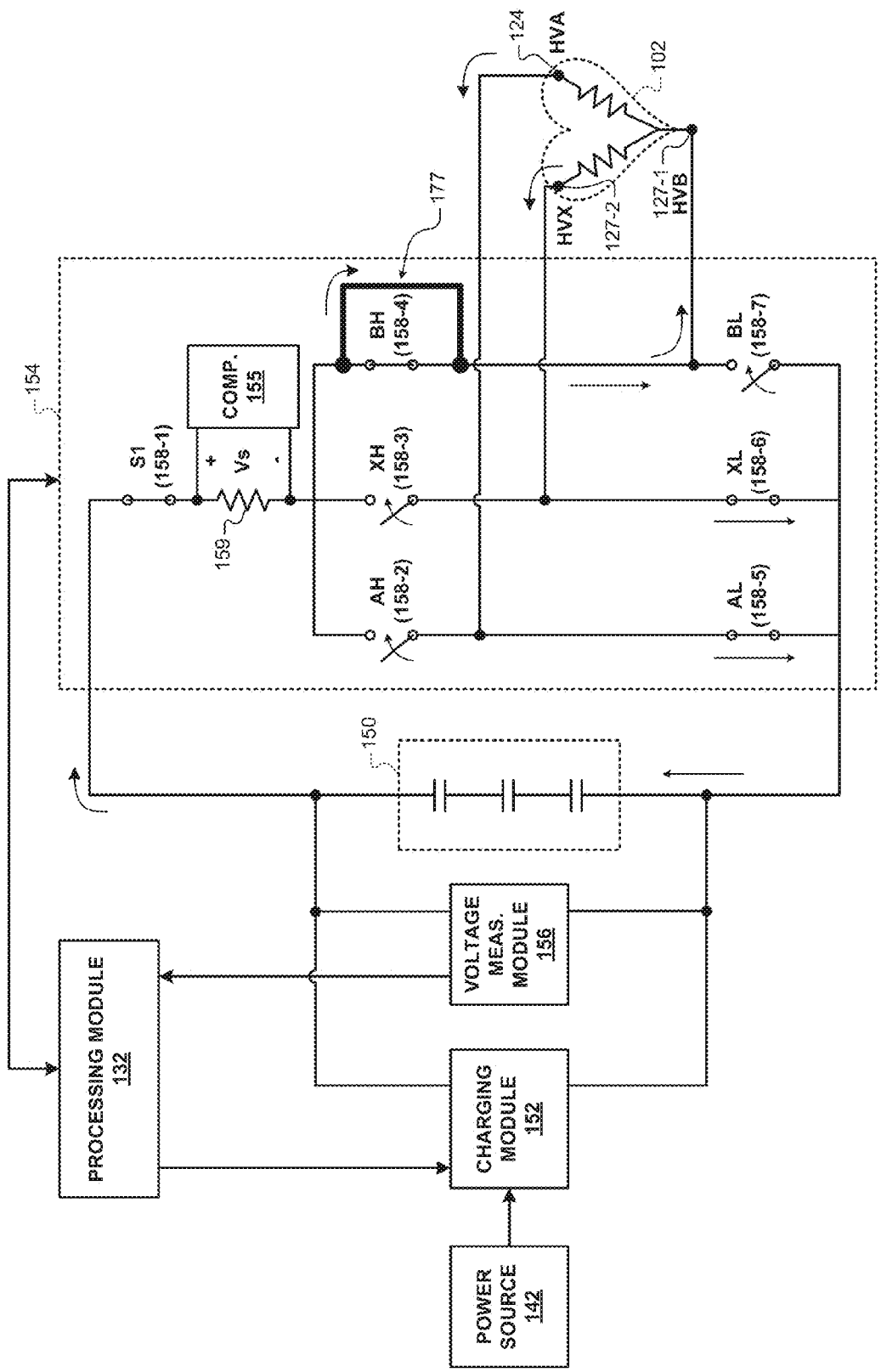
FIG. 16 is a schematic that illustrates using a short circuit fault to deliver high-energy therapy.
Figure 17:
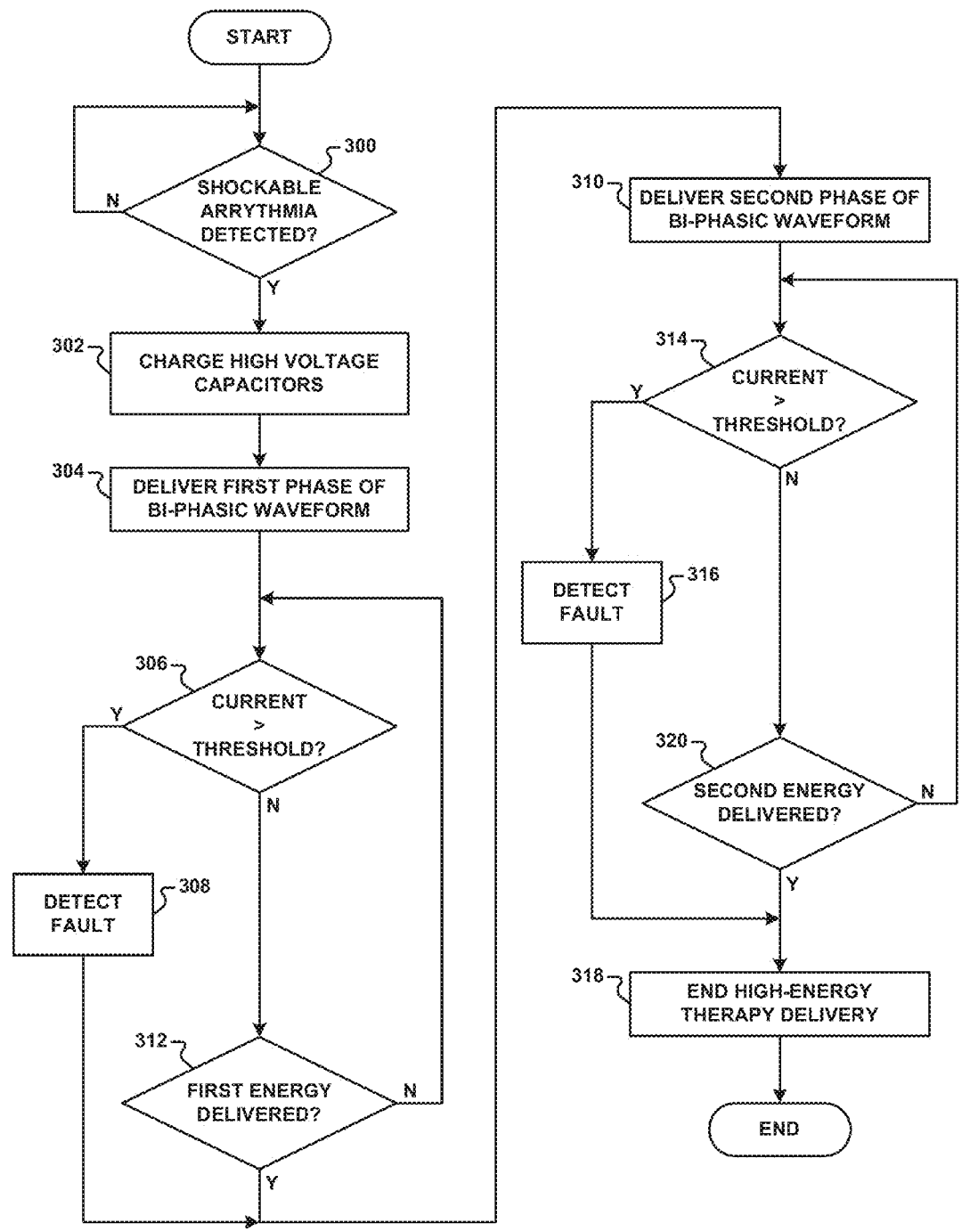
FIG. 17 is a flowchart that illustrates an example method for detecting short circuit faults during delivery of high-energy therapy using a biphasic waveform.
Figure 18:
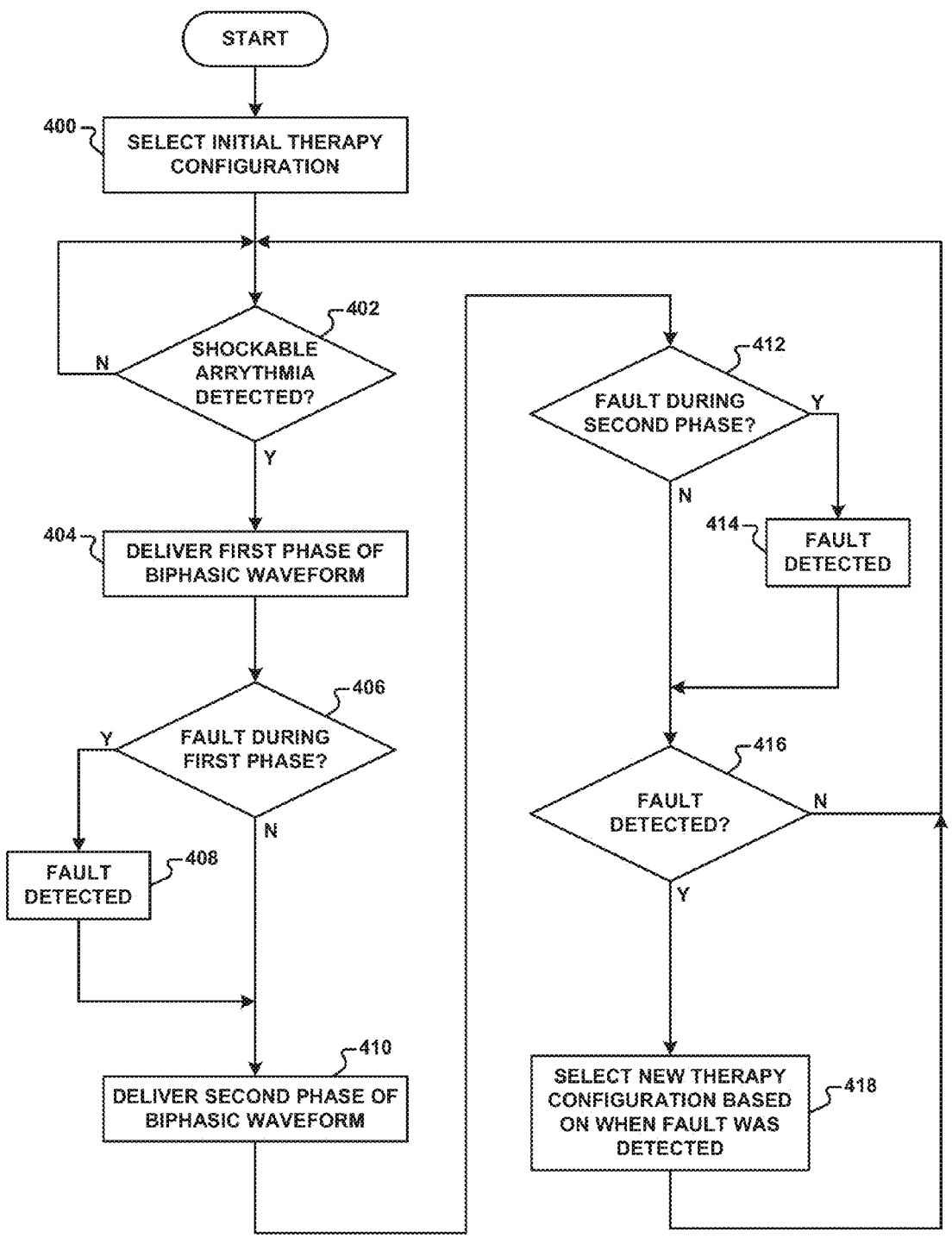
FIG. 18 is a flowchart that illustrates an example method for selecting new therapy configurations in response to detection of a short circuit fault.
Figure 19:
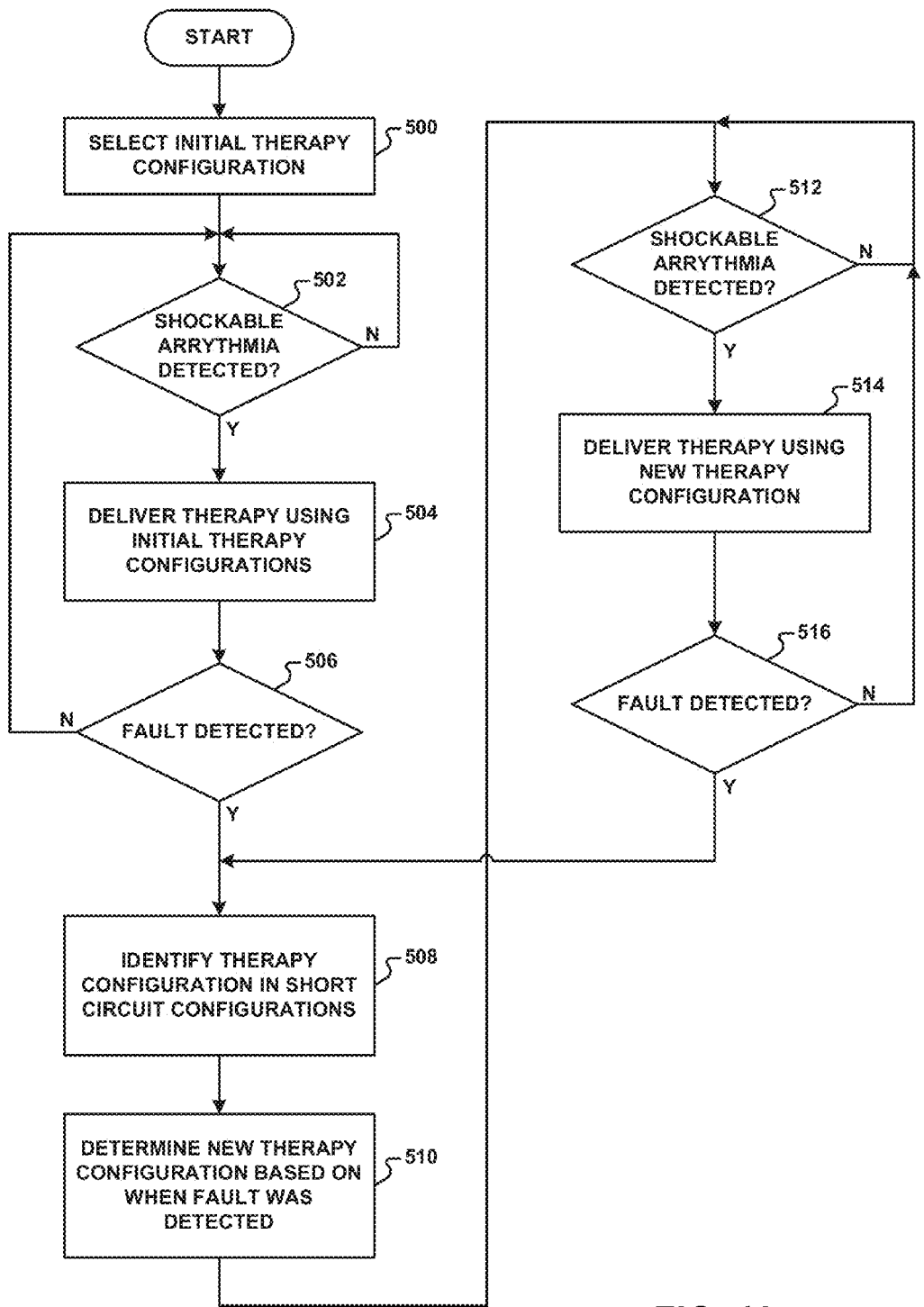
FIG. 19 is a flowchart that illustrates another example method for selecting new therapy configurations in response to detection of short circuit faults.
Figure 20:
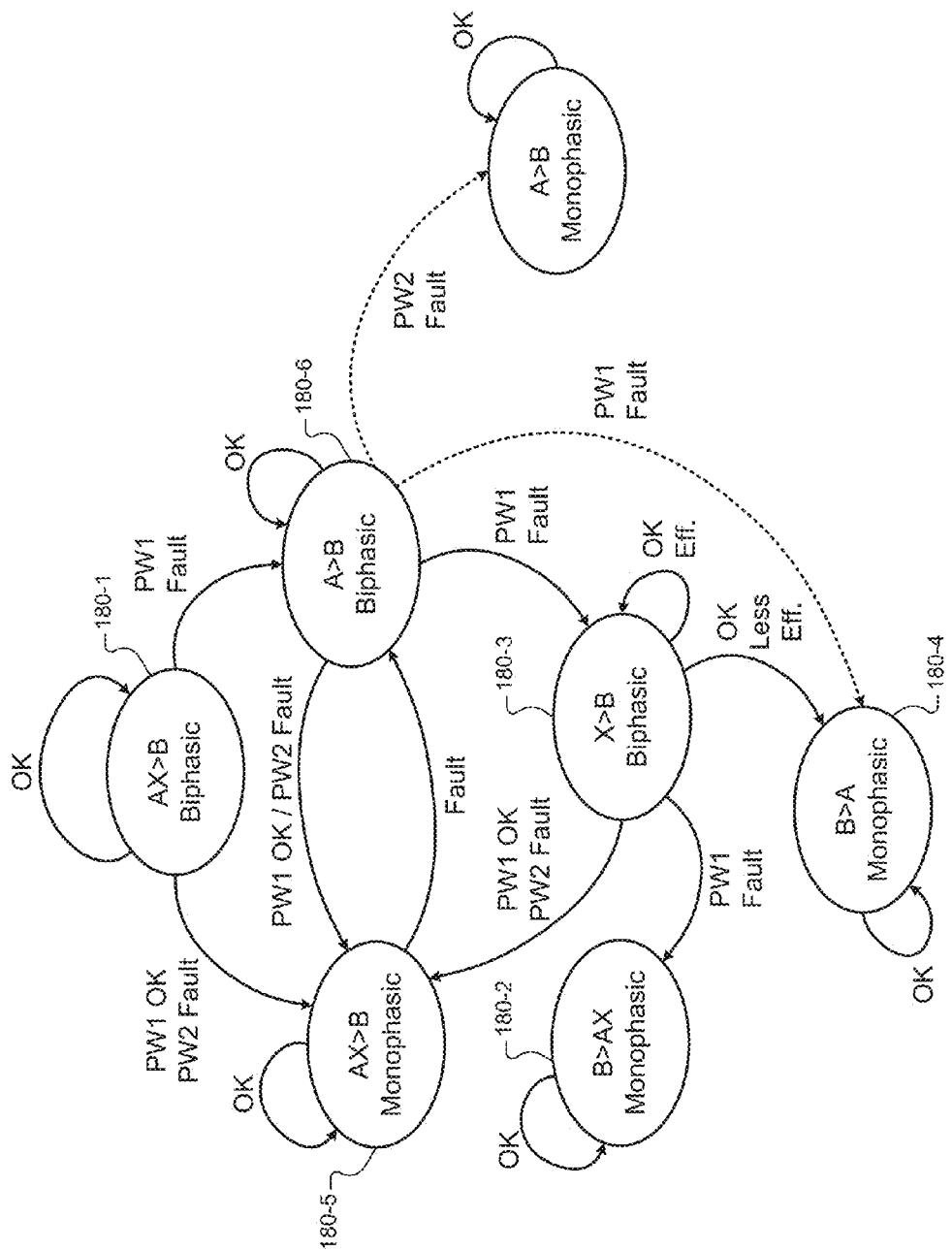
FIG. 20 is a state diagram that graphically illustrates example short circuit therapy configurations that may be selected by the IMD of FIG. 1 in response to detection of a short circuit fault.

FIGS. 1-2 show an example system including an IMD that may deliver high-energy therapy, detect short circuit faults, and reconfigure therapy configurations in response to detection of the short circuit faults. FIG. 3 shows an example functional block diagram of the IMD of FIGS. 1-2 including a memory that stores initial therapy configurations and short circuit therapy configurations. FIG. 4 shows components of the IMD that control the delivery of high-energy therapy. FIGS. 5-9 illustrate biphasic and monophasic waveforms, the switching configurations used to deliver the waveforms, and a method for delivering the waveforms. FIGS. 10-16 show schematics of example short circuit faults. FIGS. 17-19 show methods for detecting short circuit faults and reconfiguring therapy configurations in response to detection of the short circuit faults. FIG. 20 shows a state diagram that describes how an IMD may transition between various short circuit therapy configurations based on when short circuit faults are detected during delivery of high-energy therapy. FIG. 21 shows a table that describes the possible causes of potential short circuit faults in the IMD during delivery and lists potential therapy reconfigurations that may be used to overcome the potential faults.

FIG. 1 shows an example system 100 that may be used to diagnose conditions of and provide therapy to a heart 102 of a patient 104. System 100 includes an IMD 106. For example, IMD 106 may be an implantable pacemaker, cardioverter, and/or defibrillator that monitors electrical activity of heart 102 and provides electrical stimulation to heart 102.

IMD 106 includes a housing 108 and a connector block 110. Housing 108 and connector block 110 may form a hermetic seal that protects components of IMD 106. IMD 106 is coupled to leads 112, 114, and 116 via connector block 110. Leads 112, 114, 116 extend into heart 102. Right ventricular lead 114 extends into right ventricle 118. Left ventricular coronary sinus lead 116 extends into the coronary sinus to a region adjacent to the free wall of left ventricle 120. Right atrial lead 112 extends into right atrium 122.

Housing 108 may enclose an electrical sensing module that monitors electrical activity of heart 102, and may also enclose a signal generator module that generates therapeutic stimulation, such as cardiac pacing pulses, ATP therapy, cardioversion therapy, and/or defibrillation therapy. Leads 112, 114, 116 are coupled to the signal generator module and the electrical sensing module of IMD 106 via connector block 110.

FIG. 2 shows a more detailed view of IMD 106 and leads 112, 114, 116. IMD 106 includes a housing electrode 124, which may be referred to as HVA electrode 124 or can electrode 124, which may be formed integrally with an outer surface of housing 108 of IMD 106 or otherwise coupled to housing 108. Although a single housing electrode 124 is illustrated in FIGS. 1-2, IMD 106 may include more or less than a single housing electrode 124.

Leads 112, 114, 116 include electrodes 126-1 to 126-6 (collectively "electrodes 126"). Lead 114 includes bipolar electrodes 126-1, 126-2 which are located in right ventricle 118. Lead 116 includes bipolar electrodes 126-3, 126-4 which are located in coronary sinus 128. Lead 112 includes bipolar electrodes 126-5, 126-6 which are located in right atrium 122. Electrodes 126-1, 126-3, 126-5 may take the form of ring electrodes. Electrodes 126-2, 126-4, 126-6 may take the form of, for example, helix tip electrodes or small circular electrodes at the tip of a tined lead or other fixation element. Lead 114 includes elongated electrodes 127-1, 127-2 (collectively "electrodes 127") which may be coil electrodes. Electrode 127-1 may be referred to as HVB electrode 127-1 or as a right ventricular coil (RVC) electrode, and electrode 127-2 may be referred to as HVX electrode 127-2 or as a superior vena cava (SVC) coil electrode. Although three leads 112, 114, 116 are illustrated, systems according to the present disclosure may be implemented using more or less than 3 leads. Additionally, systems according to the present disclosure may be implemented using additional or fewer electrodes than illustrated in FIGS. 1-2, e.g. such as one or more epicardial patch electrodes or coronary sinus electrodes.

IMD 106 may sense electrical activity of heart 102 and/or deliver electrical stimulation to heart 102 via electrodes 124, 126, 127. IMD 106 may sense electrical activity using any combination of electrodes 124, 126, 127. For example, IMD 106 may sense electrical activity via any bipolar combination of electrodes 126, 127. Furthermore, any of electrodes 126, 127 may be used for unipolar sensing in combination with housing electrode 124. IMD 106 may deliver pacing pulses using a unipolar or bipolar combination of electrodes 124, 126, 127. IMD 106 may deliver high-energy therapy (e.g., cardioversion pulses and/or defibrillation pulses) to heart 102 via any combination of elongated electrodes HVB 127-1, HVX 127-2, and housing electrode HVA 124.

Using the signal generator module and the electrical sensing module, IMD 106 may provide pacing pulses to heart 102 based on the electrical signals sensed within heart 102. IMD 106 may also provide ATP therapy, cardioversion, and/or defibrillation therapy to heart 102 based on the electrical signals sensed within heart 102. For example, IMD 106 may detect an arrhythmia of heart 102, such as VT/VF, and deliver ATP therapy, cardioversion, or defibrillation therapy to heart 102 in response to the detection of VT/VF.

Referring back to FIG. 1, system 100 may include a programmer 130. Programmer 130 may be a handheld computing device, desktop computing device, a networked computing device, etc. Programmer 130 may include a computer-readable storage medium having instructions that cause a processor of programmer 130 to provide the functions attributed to programmer 130 in the present disclosure. Programmer 130 may include a telemetry head (not shown). IMD 106 and programmer 130 may wirelessly communicate with one another, e.g., transfer data between one another, via the telemetry head. For example, IMD 106 may send data to programmer 130, and programmer 130 may retrieve data stored in IMD 106 and/or program IMD 106.

Data retrieved from IMD 106 using programmer 130 may include cardiac EGMs stored by IMD 106 that indicate electrical activity of heart 102 and marker channel data that indicates the occurrence and timing of sensing, diagnosis, and therapy events associated with IMD 106. Additionally, data may include information regarding the performance or integrity of IMD 106 or other components of diagnostic system 100, such as leads 112, 114, 116, or a power source of IMD 106. For example, data may include information regarding whether short circuit faults were detected during delivery of high-energy therapy, and in some examples, which therapy configurations resulted in detection of short circuit faults. Data transferred to IMD 106 using programmer 130 may include, for example, values for operational parameters, electrode vectors used to deliver high-energy therapy, waveforms used for delivery of high-energy therapy, a total amount of energy used during high-energy therapy, and the distribution of the total energy among the phases of delivery for a biphasic defibrillation waveform.

FIG. 3 shows a functional block diagram of an example IMD 106. IMD 106 includes a processing module 132, memory 134, a signal generator module 136, an electrical sensing module 138, a communication module 140, and a power source 142, such as a battery, e.g., a rechargeable or non-rechargeable battery. In some examples, IMD 106 may include one or more sensors (e.g., sensor 144) with which processing module 132 may communicate. For example, sensor 144 may comprise at least one of a motion sensor (e.g., an accelerometer or piezoelectric element) and a heart sound sensor. Processing module 132 may determine, for example, an activity level of patient 104 and a heart rate of patient 104 based on data measured by sensor 144.

Modules included in IMD 106 represent functionality that may be included in IMD 106 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Processing module 132 may communicate with memory 134. Memory 134 may include computer-readable instructions that, when executed by processing module 132, cause processing module 132 to perform the various functions attributed to processing module 132 herein. Memory 134 may include any volatile, non-volatile, magnetic, or electrical media, such as RAM, ROM, NVRAM, EEPROM, Flash memory, or any other digital media.

Processing module 132 may communicate with signal generator module 136 and electrical sensing module 138. Signal generator module 136 and electrical sensing module 138 are electrically coupled to electrodes 126, 127 of leads 112, 114, 116 and housing electrode 124. Electrical sensing module 138 is configured to monitor signals from electrodes 124, 126, 127 in order to monitor electrical activity of heart 102. Electrical sensing module 138 may selectively monitor any bipolar or unipolar combination of electrodes 124, 126, 127.

Signal generator module 136 may generate and deliver electrical stimulation therapy to heart 102 via electrodes 124, 126, 127. Electrical stimulation therapy may include at least one of pacing pulses, ATP therapy, cardioversion therapy, and defibrillation therapy. Processing module 132 may control signal generator module 136 to deliver electrical stimulation therapy to heart 102 according to one or more therapy programs, which may be stored in memory 134. For example, processing module 132 may control signal generator module 136 to deliver pacing pulses to heart 102 based on one or more therapy programs and signals received from electrical sensing module 138. In other examples, processing module 132 may control signal generator module 136 to deliver at least one of ATP therapy, cardioversion therapy, and defibrillation therapy when processing module 132 detects a tachyarrhythmia. For example, in the event that processing module 132 detects a tachyarrhythmia, processing module 132 may load an ATP regimen from memory 134, and control signal generator module 136 to implement the ATP regimen. In other examples, processing module 132 may implement a cardioversion regimen or a defibrillation regimen upon detection of a tachyarrhythmia.

Communication module 140 includes any suitable hardware, firmware, software or any combination thereof for communicating with another device, such as programmer 130 and/or a patient monitor. Under the control of processing module 132, communication module 140 may receive downlink telemetry from and send uplink telemetry to programmer 130 and/or a patient monitor with the aid of an antenna (not shown) in IMD 106.

Processing module 132 may receive raw data (e.g., digitized electrogram data) from electrical sensing module 138 and detect cardiac events based on the raw data. For example, processing module 132 may analyze the raw data and detect arrhythmias (e.g., VT/VF) using any suitable arrhythmia detection algorithm. In one example, processing module 132 may detect tachyarrhythmias using a rate-based detection algorithm in which processing module 132 monitors R-R intervals and identifies a tachyarrhythmia when a predetermined ratio of R-R intervals are shorter than a threshold interval. In some examples, processing module 132 may perform further analysis of tachyarrhythmias using rate information. For example, processing module 132 may characterize tachyarrhythmias based on the range of values in which the intervals fall, the stability of the intervals, and the average or median values of the intervals. In some examples, processing module 132 may confirm the presence of detected tachyarrhythmias using other algorithms such as a template matching algorithms.

Processing module 132 may instruct signal generator module 136 to deliver high-energy therapy (e.g., defibrillation pulses or cardioversion pulses) in response to detection of shockable arrhythmias (e.g., VT/VF). Delivery of high-energy therapy by signal generator module 136 to heart 102 may correct the shockable arrhythmia and return heart 102 to a normal rhythm. In examples where the detected shockable arrhythmia is not corrected, processing module 132 control delivery of subsequent high-energy therapies.

Signal generator module 136 includes circuits that deliver the high-energy therapy to heart 102 and monitor the delivery of the high-energy therapy while the high-energy therapy is being delivered. FIG. 3 shows a high-level functional block diagram of signal generator module 136. Signal generator module 136 may include an energy storage device for storing energy to be delivered during the high-energy therapy. The energy storage device described herein includes one or more capacitors, hereinafter "high-voltage capacitors 150," that are used to store electrical charge for delivery to heart 102 during high-energy therapy. Although the energy storage device used to store energy for delivery of high-energy therapy is described herein as one or more capacitors, other energy storage devices may be implemented.

Signal generator module 136 may also include a charging module 152, a switching circuit 154, and a voltage measuring module 156. Charging module 152 may charge high voltage capacitors 150 in response to instructions from processing module 132, e.g., instructions provided by processing module 132 in response to detection of a shockable arrhythmia. Voltage measuring module 156 may measure the voltage across high-voltage capacitors 150 in order to determine a level of charge present on high-voltage capacitors 150. Switching circuit 154 may be controlled by processing module 132 in order to deliver the high-energy therapy to heart 102 via leads 112, 114, 116. In other words, under control of processing module 132, switching circuit 154 may connect high-voltage capacitors 150 to electrodes 124, 127 in order to transfer energy from high-voltage capacitors 150 to heart 102.

Signal generator module 136 may include a comparator module 155 that indicates an amount of current being delivered from high-voltage capacitors 150 during the delivery of high-energy therapy. For example, comparator module 155 may indicate to processing module 132 when the amount of current being delivered from high-voltage capacitors 150 is greater than a threshold amount of current. Delivery of an amount of current that is greater than the threshold current during delivery of high-energy therapy may indicate that a short circuit fault is present in the delivery pathway. Accordingly, processing module 132 may detect a short circuit fault when comparator module 155 indicates that the amount of current being delivered by high-voltage capacitors 150 is greater than the threshold amount of current.

Typical operation of IMD 106 with respect to the delivery of high-energy therapy, e.g., without detection of short circuit faults, is described hereinafter with respect to the functional block diagrams of FIGS. 4-8 and the method of FIG. 9.

FIG. 4 shows components of IMD 106 that control charging of high-voltage capacitors 150, monitoring of the voltage across high-voltage capacitors 150, delivery of high-energy therapy to heart 102, and detection of short circuit faults. Processing module 132, upon detection of a shockable arrhythmia (e.g., VT/VF) may instruct charging module 152 to charge high-voltage capacitors 150 using energy from power source 142. High-voltage capacitors 150 may store the energy that is to be subsequently delivered to heart 102 during delivery of the high-energy therapy. Charging module 152 may include a DC-to-DC converter circuit that converts a source of direct current from one voltage level to another. In some examples, the DC-to-DC converter may have a flyback topology.

Voltage measuring module 156 may measure the voltage across high-voltage capacitors 150 while high-voltage capacitors 150 are being charged by charging module 152. The voltage measured across high-voltage capacitors 150 is indicated by +/−Vcap at 157 in FIG. 4. The voltage measured across high-voltage capacitors 150 may indicate an amount of electrical energy stored on high-voltage capacitors 150. Voltage measuring module 156 may indicate the measured voltage to processing module 132. Processing module 132 may determine an amount of energy stored by high-voltage capacitors 150 based on the voltage indicated by voltage measuring module 156. For example, processing module 132 may include a look-up table (e.g., voltage vs. energy) or an equation that processing module 132 may use to determine the amount of energy stored by high-voltage capacitors 150 based on the voltage measured across high-voltage capacitors 150.

In some examples, voltage measuring module 156 may include analog-to-digital conversion circuits that measure the voltage across high-voltage capacitors 150 and generate a digital value that indicates the measured voltage. In these examples, processing module 132 may determine the voltage across high-voltage capacitors 150 based on the digital value received from voltage measuring module 156.

Processing module 132 may instruct charging module 152 to stop charging high-voltage capacitors 150, e.g., disconnect from high-voltage capacitors 150, when the voltage across high-voltage capacitors 150 reaches a threshold voltage that indicates that high-voltage capacitors 150 have been charged with an amount of electrical energy to be used during delivery of high-energy therapy. The total amount of energy to be delivered during high-energy therapy may be programmed into memory 134 by a clinician, e.g., using programmer 130. In some examples, processing module 132 may determine the threshold voltage based on the programmed energy. Based on the determined threshold voltage, processing module 132 may determine when the programmed energy is stored on high-voltage capacitors 150 during charging. The threshold voltage that indicates that high-voltage capacitors 150 are charged to a state in which high-voltage capacitors 150 may deliver the high-energy therapy may be indicated as $V_0$ in FIG. 5 and FIG. 8. In terms of FIG. 4, processing module 132 may instruct charging module 152 to charge high-voltage capacitors 150 until the voltage Vcap 157 across high-voltage capacitors 150 reaches the threshold voltage $V_0$.

After high-voltage capacitors 150 are charged up to the threshold voltage $V_0$ and processing module 132 instructs charging module 152 to stop charging high-voltage capacitors 150, processing module 132 controls switching circuit 154 to deliver the high-energy therapy to heart 102. Switching circuit 154 includes switches 158-1, 158-2, . . . , and 158-7 (collectively "switches 158"). Each of switches 158, when functional, may operate in one of an "open state" or a "closed state." Each of switches 158 may act as an open circuit (i.e., a high impedance) when operating in the open state. Each of switches 158 may act as a short circuit (i.e., a low impedance) when operating in the closed state. In some examples, a switch operating in the "closed state" may be referred to as operating in the "on state" or may be referred to as "turned on." In a similar manner, a switch operating in the "open state" may be referred to as operating in the "off state" or may be referred to as "turned off."

When switches 158 are functional, the state of switches 158 (i.e., open or closed) may be controlled by processing module 132. The collective state of all switches 158 may be referred to as a "switching configuration" of switching circuit 154. Accordingly, processing module 132 may control the switching configuration of switching circuit 154. In some examples, one or more of switches 158 may malfunction. A malfunction in a switch may refer to a scenario where the actual behavior of the switch is different from the behavior of the switch that was commanded by processing module 132. In some examples, a malfunctioning switch will remain in an open state when instructed to close. In other examples, a malfunctioning switch will remain in a closed state when instructed to open. In other words, a malfunctioning switch may be stuck in one of the open or closed states. A malfunctioning switch may not necessarily behave in either a strictly open state (i.e., an open circuit) or a strictly closed state (i.e., as a short circuit), but may behave as an impedance that has a value somewhere between the impedances of the closed and open states.

In examples where a switch is instructed to open by processing module 132, but instead the switch presents a low impedance (e.g., a short circuit) upon receipt of the instruction, the switch may be said to have a short circuit fault. In some examples, a switch may malfunction in such a way that it presents a permanently low impedance (e.g., a short circuit) regardless of the instructions received from processing module 132. Detection of a short circuit fault in a switch is described hereinafter.

Switches 158 may include one or more types of switching technologies. Switches 158 may generally represent any type of switching device that may be instructed to operate in open/closed states and that may operate under conditions (e.g., voltages/currents) present during delivery of high-energy therapy. In some examples, switches 158 may be silicon-controlled rectifier (SCR) devices. In examples where switches 158 include SCR devices, processing module 132 may apply a control voltage to the SCR devices to turn on the SCR devices. In other examples, switches 158 may include types of switches other than SCR devices. For example, switches 158 may include power metal-oxide-semiconductor field-effect-transistors (MOSFETs). In examples where switches 158 include power MOSFETs, processing module 132 may control a gate voltage applied to switches 158 to control the states of switches 158. Although switches 158 may include SCR devices and power MOSFET devices, in other examples, switches 158 may include other types of high power switching devices, such as insulated-gate bipolar transistors (IGBTs), TRIACS, thyristors, or other power switching devices.

Switching circuit 154 includes a sense resistor 159 that receives the current being delivered to switching circuit 154 by high-voltage capacitors 150 during delivery of high-energy therapy. The value of sense resistor 159 may be relatively small, so as not to present a load that may interfere with delivery of the high-energy therapy. A voltage Vs is generated across sense resistor 159 when current is being delivered to heart 102 during delivery of high-energy therapy. The voltage Vs may indicate the amount of current being delivered by high-voltage capacitors 150. Comparator module 155 may compare the voltage Vs to a threshold voltage. The threshold voltage and the sense resistor may be selected based on an expected amount of current that may pass through switching circuit 154 when a short circuit fault is present. For example, the threshold voltage and sense resistor may be selected such that a threshold amount of current, indicative of a short circuit fault, may generate the threshold voltage across sense resistor 159. Accordingly, comparator module 155 may indicate to processing module 132 that a short circuit fault is present when the voltage Vs is greater than the threshold voltage. Comparator module 155 may indicate to processing module 132 that a short circuit fault is not present when the voltage Vs is less than the threshold voltage. Comparator module 155 may be a circuit that indicates a digital value (e.g., high/low) to processing module 132 based on comparison of the voltage Vs to the threshold voltage. Processing module 132 may detect a short circuit fault during delivery of high-energy therapy when comparator module 155 indicates to processing module 132 that a short circuit fault is present. Accordingly, processing module 132 may detect a short circuit fault based on the amount of current being delivered by high-voltage capacitors 150 during delivery of high-energy therapy.

Generally, processing module 132 may control delivery of high-energy therapy to heart 102 based on a variety of parameters. The parameters that specify delivery of high-energy therapy may be referred to herein as high-energy therapy configurations, or simply therapy configurations. As described above, therapy configurations may specify an electrode vector to be used during therapy and an electrical waveform (e.g., biphasic or monophasic) to be delivered by the electrode vector.

Memory 134 may store the various therapy configurations that may be implemented by processing module 132 in order to deliver high-energy therapy. Processing module 132 may, in response to detection of a shockable arrhythmia, retrieve a therapy configuration from memory 134, and control the delivery of high-energy therapy based on the information included in the retrieved therapy configuration. As illustrated in FIG. 3, memory 134 may include two sets of therapy configurations, initial therapy configurations 160, and short circuit therapy configurations 162.

Initially, processing module 132 may control the delivery of high-energy therapy using initial therapy configurations 160. Initial therapy configurations 160 may define a pattern of selection of therapy configurations to be used by processing module 132 in scenarios where processing module 132 has not previously detected a short circuit fault during delivery of high-energy therapy. Accordingly, processing module 132 may control delivery of high-energy therapy according to initial therapy configurations 160 in response to detection of a shockable arrhythmia in scenarios where processing module 132 has not yet detected a short circuit fault.

Initial therapy configurations 160 may define a pattern of selection of therapy configurations that may be used by processing module 132 during attempts to treat a detected shockable arrhythmia. For example, processing module 132 may initially attempt to treat a shockable arrhythmia using a first therapy configuration of initial therapy configurations 160. If successful in treating the shockable arrhythmia, processing module 132 may return to monitoring the rhythm of heart 102. If unsuccessful in treating the shockable arrhythmia, e.g., if the shockable arrhythmia is not corrected, processing module 132 may select a second therapy configuration of initial therapy configurations 160 to treat the shockable arrhythmia. In this manner, processing module 132 may continue to select consecutive therapy configurations from initial therapy configurations 160 in order to attempt to treat a shockable arrhythmia in different ways until a successful treatment is found, e.g., until the shockable arrhythmia is corrected.

Initial therapy configurations 160 may be programmed into memory 134 prior to implantation, e.g., as factory default settings or programmed by a clinician. In other examples, initial therapy configurations 160 may be updated by a clinician using programmer 130 after IMD 106 is implanted. Initial therapy configurations 160 may define a variety of different electrode vector and waveform combinations, as well as different amounts of energies to be delivered during high-energy therapy.

Processing module 132 may control delivery of high-energy therapy according to initial therapy configurations 160 until a short circuit fault is detected during delivery of high-energy therapy according to initial therapy configurations 160. Upon detection of a short circuit fault during delivery of high-energy therapy, processing module 132 may begin delivering high-energy therapy according to short circuit therapy configurations 162 stored in memory 132. Short circuit therapy configurations 162 may define the selection of therapy configurations used by processing module 132 after a short circuit fault is detected during delivery of high-energy therapy. Accordingly, after detection of a short circuit fault, processing module 132 may control delivery of high-energy therapy according to short circuit therapy configurations 162 in response to detection of a shockable arrhythmia.

Short circuit therapy configurations 162 may represent a plurality of different therapy configurations (i.e., N different therapy configurations). Each of the N therapy configurations 164-1, 164-2, . . . , 164-N (collectively "N therapy configurations 164") may define an electrode vector (e.g., AX>B, A>X, etc.), a waveform (e.g., biphasic/monophasic), and transition data. Transition data included in each of N therapy configurations 164 may define a subsequent one of the N therapy configurations to select in response to detection of a short circuit fault at the current therapy configuration. For example, if processing module 132 detects a short circuit fault while using first therapy configuration 164-1, processing module 132 may select a subsequent therapy configuration to use by looking at the transition data that is associated with the current therapy configuration 164-1. The transition data of first therapy configuration 164-1 may indicate that processing module 132 should transition to second therapy configuration 164-2 in response to detection of a short circuit fault during delivery according to first therapy configuration 164-1. In this case, processing module 132 may then control high-energy therapy delivery according to second therapy configuration 164-2. If a fault is then detected by processing module 132 when using second therapy configuration 164-2, processing module 132 may set the next therapy configuration to the therapy configuration indicated by the transition data of second therapy configuration 164-2. In this manner, processing module 132 may determine a subsequent therapy configuration to use for the delivery of high-energy therapy based on the current therapy configuration in which a short circuit fault is detected.

In addition to determining subsequent therapy configurations based on a current therapy configuration in which a short circuit fault is detected, processing module 132 may also make the subsequent therapy selection based when the short circuit fault was detected during the delivery of high-energy therapy. In other words, processing module 132 may select a subsequent therapy configuration based on the current therapy configuration in which a fault is detected and based on when the detected fault occurred during delivery of high-energy therapy according to the current therapy configuration.

The transition data may specify the subsequent therapy configuration based on when the short circuit fault was detected during delivery according to the current therapy configuration. For example, the transition data associated with first therapy configuration 164-1 may instruct processing module 132 to deliver therapy according to second therapy configuration 164-2 if a short circuit fault is detected during the first phase of the biphasic waveform of first therapy configuration 164-1, and the transition data associated with first therapy configuration 164-1 may instruct processing module 132 to deliver therapy according to the Nth therapy configuration 164-N if a short circuit fault is detected during the second phase of the biphasic waveform of first therapy configuration 164-1. Example selection of therapies according to short circuit therapy configurations 162 is described further with respect to the state diagram of FIG. 20.

Although initial therapy configurations 160 and short circuit therapy configurations 162 are illustrated as separate therapy configurations, some therapy configurations included in initial therapy configurations 160 may be the same as some therapy configurations included in short circuit therapy configurations 162. The illustration of the therapy configurations 160, 162 as separate is meant to convey the concept that processing module 132 may follow different paths when selecting therapy configurations, depending on whether a short circuit fault has been detected.

An electrode vector specified by a therapy configuration may include two or three of electrodes 124, 127. In some examples, three electrodes may be used to deliver high-energy therapy, while in other examples, less than three electrodes may be used to deliver high-energy therapy, i.e., in some examples, only 2 electrodes may be used to deliver therapy while a third electrode does not deliver therapy or is not physically present in the system.

Electrodes used for delivery of defibrillation therapy are described and illustrated herein as electrodes HVA 124, HVB 127-1, and HVX 127-2. Electrode HVA 124 is an electrode on housing 108, and may be referred to as a "can electrode" in some examples. Electrode HVB 127-1 is a defibrillation coil in right ventricle 118. Electrode HVX 127-2 is an additional electrode on lead 114 or may be part of an additional lead or electrode in the system. Although electrodes HVA 124, HVB 127-1, and HVX 127-2 are described herein as electrodes used for the delivery of high-energy therapy, it is contemplated that other electrode configurations different from those illustrated and described herein may be used for delivery of high-energy therapy.

Electrode vectors may be described and illustrated using a notation that includes the greater-than symbol ">" to indicate the direction of current between electrodes. For example, electrode vector "AX>B" indicates that the direction of current during therapy delivery is from HVA electrode 124 and HVX electrode 127-2 to HVB electrode 127-1. In some examples, e.g., during biphasic or multiphasic delivery, the direction of current may be reversed or altered based on the phase of delivery. Electrode vectors described herein that include three electrodes include "AX>B" and "B>AX." Electrode vectors described herein that include only two electrodes include "A>B", "B>A", "X>B", and "B>X."

Figure 5:
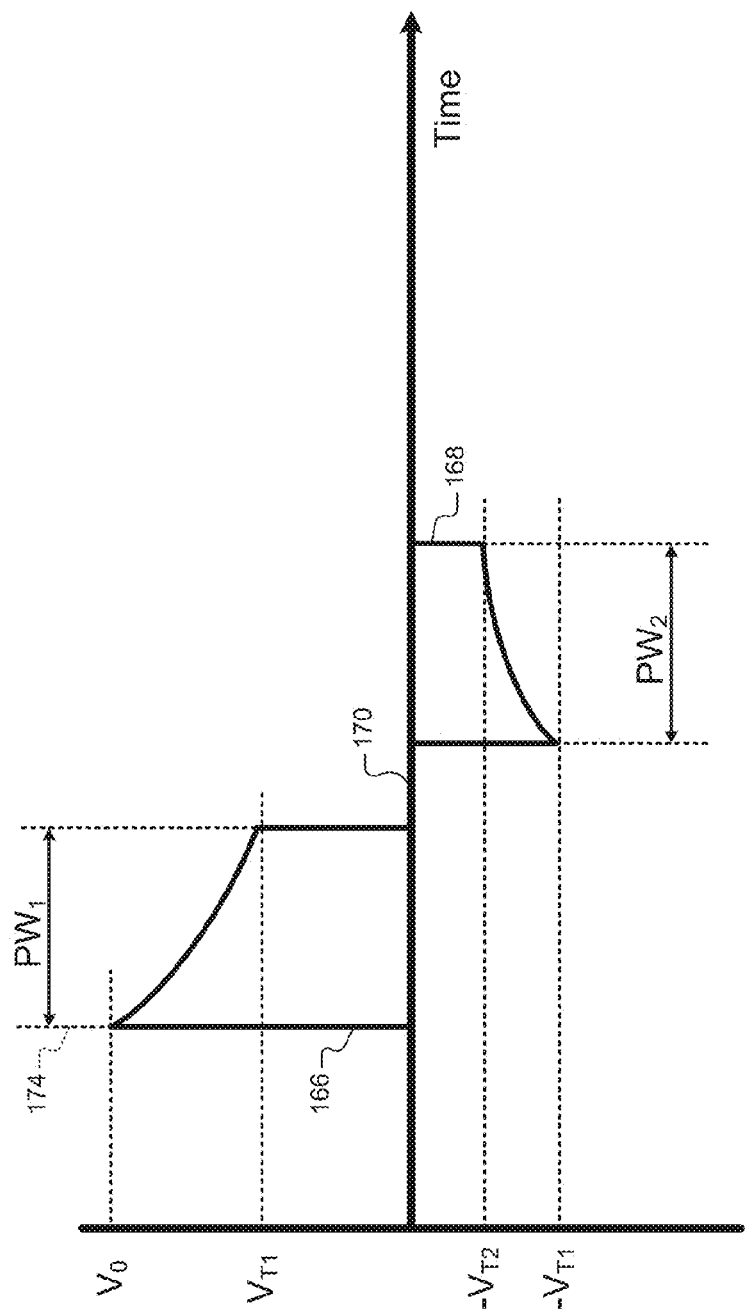
FIG. 5 shows a biphasic waveform that includes a first phase of delivery and a second phase of delivery which are separated by a transition period.
Figure 8:
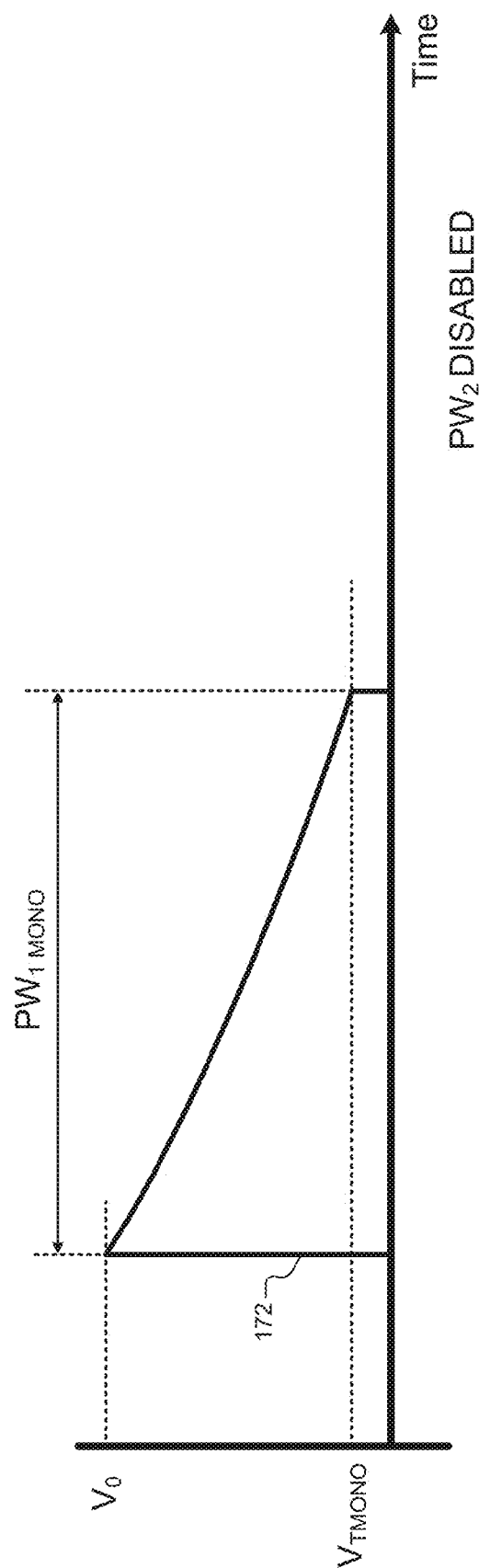
FIG. 8 shows an example monophasic waveform.

Therapy configurations may specify the type of waveform to be delivered during high-energy therapy. Processing module 132 may control switching circuit 154 to deliver the type of waveform defined by the therapy configurations 160, 162. Generally, high-energy therapy may be delivered using a biphasic waveform or a monophasic waveform. Example biphasic and monophasic waveforms are illustrated in FIGS. 5 and 8, respectively. The biphasic waveform illustrated in FIG. 5 includes a first phase 166 and a second phase 168, separated by a transition period 170. The monophasic waveform illustrated in FIG. 8 includes a single phase 172, referred to herein as a "monophasic pulse 172." Delivery of high-energy therapy according to the biphasic and monophasic waveforms is now described with respect to FIGS. 5 and 8, respectively.

Referring now to FIG. 5, a biphasic waveform includes a first phase of delivery 166 and a second phase of delivery 168, separated by a transition period 170. The biphasic waveform of FIG. 5 is illustrated as a voltage waveform vs. time. The y-axis may represent the magnitude of the voltage across high-voltage capacitors 150, while the x-axis may represent the amount of time elapsed during delivery of the biphasic waveform. Processing module 132 may start the delivery of high-energy therapy at 174. Prior to the start of high-energy therapy, charging module 152 charged high-voltage capacitors 150 to the voltage $V_0$, e.g., based on the amount of energy programmed by the clinician, as described above. Accordingly, the voltage across high-voltage capacitors 150 at the start of delivery of the high-energy therapy is set at $V_0$.

Figure 6:
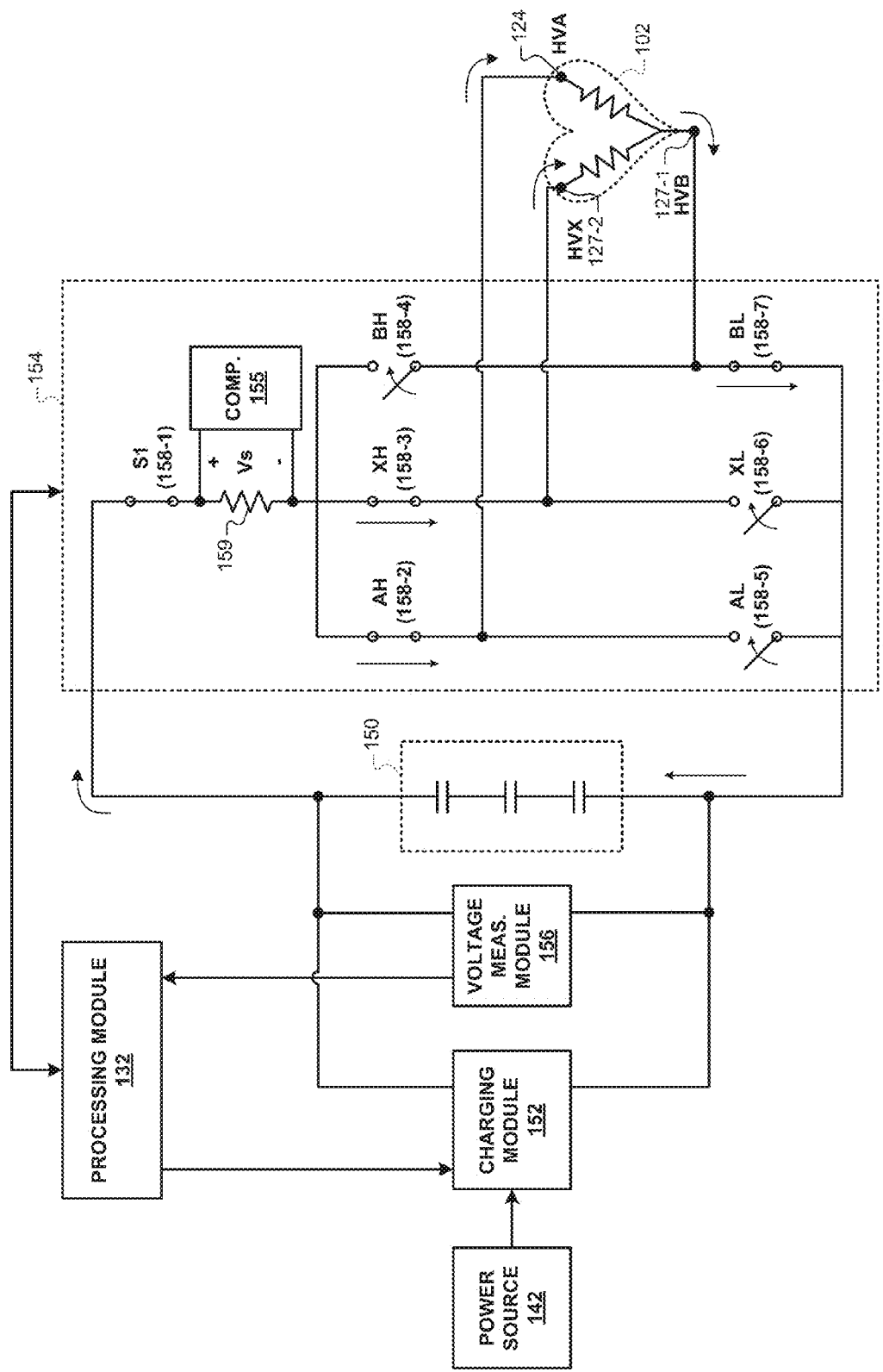
FIG. 6 is a schematic that illustrates an example switching configuration of a switching circuit that may be used to deliver a first phase of high-energy therapy.

Prior to delivery of high-energy therapy according to FIG. 5, switches 158 of switching circuit 154 may all be in the open state as illustrated in FIG. 4. Processing module 132 may instruct switching circuit 154 to change switching configurations in order to start delivery of first phase 166. FIG. 6 illustrates an example switching configuration of switching circuit 154 that may be used to deliver first phase 166 of high-energy therapy. In the example switching configuration of FIG. 6 instructed by processing module 132, first phase 166 of high-energy therapy is delivered using electrodes HVA 124, HVX 127-2, and HVB 127-1 (i.e., electrode vector AX>B). In order to deliver first phase 166, processing module 132 may instruct each of switches S1 158-1, AH 158-2, XH 158-3, and BL 158-7 to transition from the open state to the closed state.

The direction of current through switches AH 158-2, XH 158-3, BL 158-7 and heart 102 (modeled as resistors) during first phase 166 is illustrated by arrows. The voltage across high-voltage capacitors 150 may decrease during first phase 166 as current is delivered to heart 102. Voltage measuring module 156 may measure the voltage across high-voltage capacitors 150 during first phase 166. Processing module 132 may monitor the voltage measured by voltage measuring module 156 during first phase 166. Processing module 132 may determine the amount of energy delivered to heart 102 based on the change in the monitored voltage. Comparator module 155 may monitor an amount of current being delivered during first phase 166 to determine whether the amount of current indicates a short circuit fault. Processing module 132 may determine whether a short circuit fault is present during first phase 166 based on the determination made by comparator module 155.

As described above, a clinician may program a total amount of energy to be delivered during the high-energy therapy. The clinician may also program how the total amount of energy is to be distributed between first and second phases 166, 168. In some examples, the clinician may program IMD 106 to divide the total amount of programmed energy equally (e.g., 50/50) between first and second phases 166, 168. In other examples, the clinician may program IMD 106 to divide the total amount of programmed energy unequally (e.g., 60/40) between the first and second phases 166, 168. Processing module 132 may determine threshold voltages for each of the first and second phases 166, 168 based on the amount of energy to be delivered during the first and second phases 166, 168, respectively. The threshold voltages of the first and second phases 166, 168 may be used by processing module 132 as indicators that the energy for each of the first and second phases 166, 168 has been delivered.

The threshold voltages for the first and second phases 166, 168 are illustrated as $V_{T1}$ and $-V_{T2}$ in FIG. 5. Processing module 132 may determine that the amount of energy programmed for first phase 166 (i.e., the first portion of the total energy) was delivered to heart 102 when the monitored voltage across high-voltage capacitors 150 has dropped from $V_0$ to $V_{T1}$. Similarly, processing module 132 may determine that the amount of energy programmed for second phase 168 (i.e., the second portion of the total energy) was delivered to heart 102 when the monitored voltage across high-voltage capacitors 150 has dropped from $V_{T1}$ to $V_{T2}$.

Processing module 132 may control switching circuit 154 to discontinue delivery of high-energy therapy when processing module 132 determines that the voltage across high-voltage capacitors 150 has dropped to the first threshold voltage $V_{T1}$. In other words, processing module 132 may set the switching configuration of switching circuit 154 such that high-voltage capacitors 150 are disconnected from electrodes 124, 127. In some examples, processing module 132 may instruct switching circuit 150 to open all switches 158 in switching circuit 154 so that high-voltage capacitors 150 are disconnected from electrodes 124, 127. In examples where switches AH 158-2, XH 158-3, and BL 158-7 are SCR devices and switch S1 158-1 is a power MOSFET device, processing module 132 may control switch S1 158-1 to open, thereby disconnecting switches AH 158-2, XH 158-3, and BL 158-7 from high-voltage capacitors 150 and therefore setting switches AH 158-2, XH 158-3, and BL 158-7 to the open state.

With respect to FIG. 8, processing module 132 may control delivery of monophasic pulse 172 in a similar manner that processing module 132 controls delivery of first phase 166 described above. As illustrated in FIG. 8, processing module 132 may include a threshold voltage $V_{TMONO}$ that may be used by processing module 132 to determine when to discontinue therapy.

Processing module 132 may wait for a short transition period 170 after first phase 166 prior to controlling switching circuit 154 to deliver therapy according to second phase 168. In some examples, transition period 170 may be a wait on the order of approximately several milliseconds (e.g., 5 milliseconds). Processing module 132 may then control switching circuit 154 to deliver therapy according to second phase 168.

Figure 7:
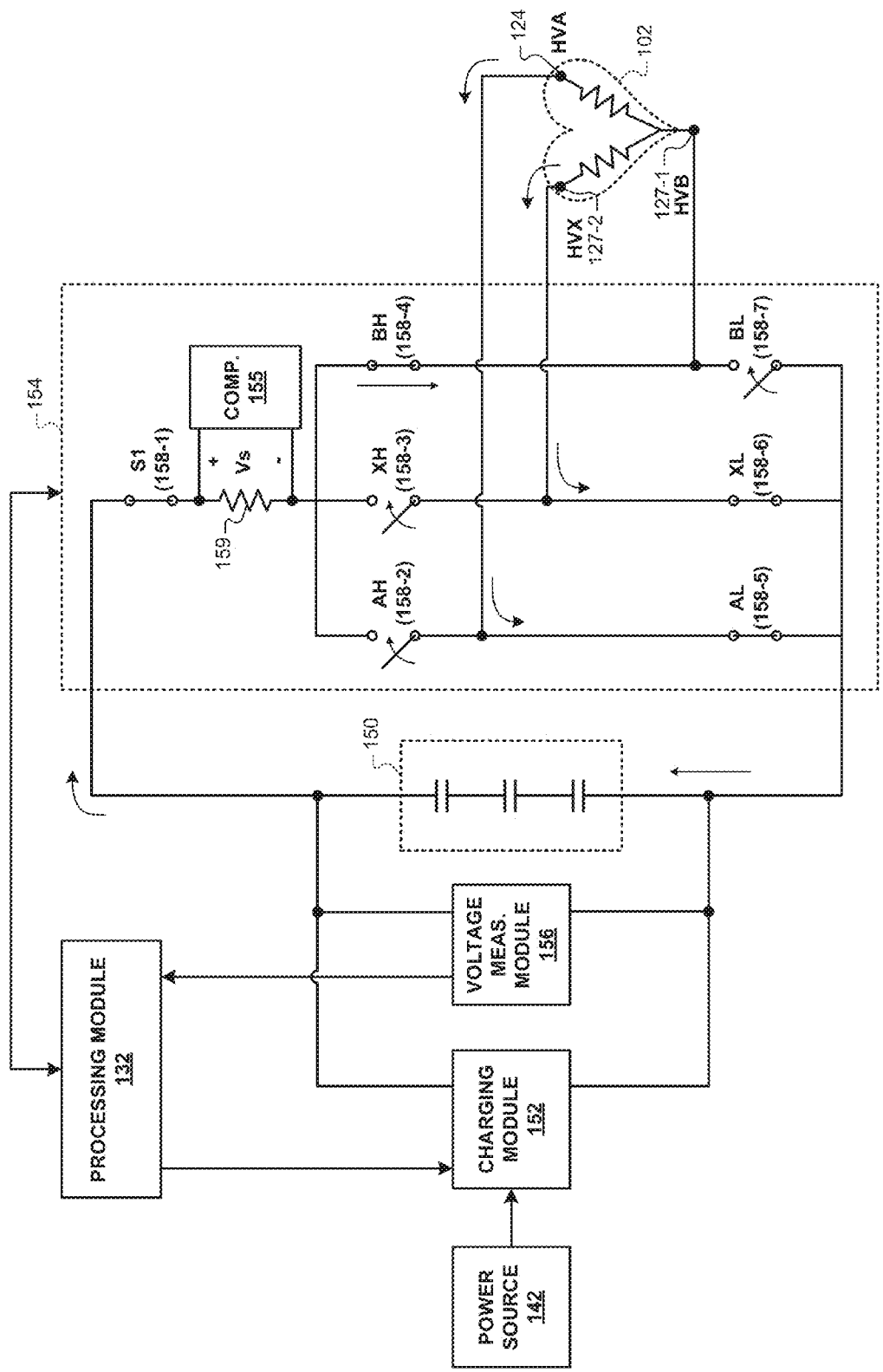
FIG. 7 is a schematic that illustrates an example switching configuration of a switching circuit that may be used to deliver a second phase of high-energy therapy.

FIG. 7 is a schematic that illustrates delivery of high-energy therapy during second phase 168. During second phase 168, processing module 132 controls switching circuit 154 to deliver energy to heart 102 in a polarity that is opposite to that delivered during first phase 166. The direction of current through switching circuit 154 and heart 102 is illustrated by arrows. In order to deliver therapy during second delivery phase 168, processing module 132 instructs switches S1 158-1, BH 158-4, AL 158-5, and XL 158-6 to close. Voltage measuring module 156 measures the voltage across high-voltage capacitors 150 during second delivery phase 168.

Referring back to FIG. 5, the voltage waveform during second phase 168 is illustrated as negative to indicate that energy is being delivered to heart 102 from high-voltage capacitors 150 in a polarity that is opposite to that delivered during first phase 166. At the start of second phase 168 of high-energy therapy, the voltage across high-voltage capacitors 150 is approximately equal to the voltage across high-voltage capacitors 150 at the end of first phase 166. For example, the voltage across high-voltage capacitors 150 at the start of second phase is illustrated as $-V_{T1}$ in FIG. 5, which is equal in magnitude to the voltage $V_{T1}$ at the end of first phase 166.

Voltage measuring module 156 measures the voltage across high-voltage capacitors 150 during second phase 168. Voltage across high-voltage capacitors 150 may decrease during second phase 168. Processing module 132 may monitor the decrease in voltage during second phase 168. Processing module 132 may control switching circuit 154 to discontinue second phase 168 when the voltage across high-voltage capacitors 150 drops to a threshold voltage that indicates that the programmed amount of energy has been delivered during second phase 168. The threshold voltage that indicates that the programmed amount of energy has been delivered is illustrated as $-V_{T2}$. Additionally, comparator module 155 may monitor an amount of current delivered during second phase 168 to determine whether the amount of current indicates a short circuit fault. Processing module 132 may determine whether a short circuit fault is present during second phase 168 based on the determination made by comparator module 155.

Processing module 132 may control switching circuit 154 to discontinue delivery of high-energy therapy when processing module 132 determines that the voltage across high-voltage capacitors 150 has dropped to the threshold voltage $-V_{T2}$ (e.g., dropped to a magnitude of $V_{T2}$). In other words, processing module 132 may set the switching configuration of switching circuit 154 such that high-voltage capacitors 150 are disconnected from electrodes 124, 127 when the voltage across high-voltage capacitors 150 has dropped to $V_{T2}$. Processing module 132 may control switching circuit 154 to stop delivery of therapy during second phase 168 by instructing all switches 158 of switching circuit 154 to open. In examples where switches BH 158-4, AL 158-5, and XL 158-6 are SCR devices and switch S1 158-1 is a power MOSFET device, processing module 132 may control switch S1 158-1 to open, thereby disconnecting switches BH 158-4, AL 158-5, and XL 158-6 from high-voltage capacitors 150 and therefore setting switches BH 158-4, AL 158-5, and XL 158-6 to the open state.

Figure 9:
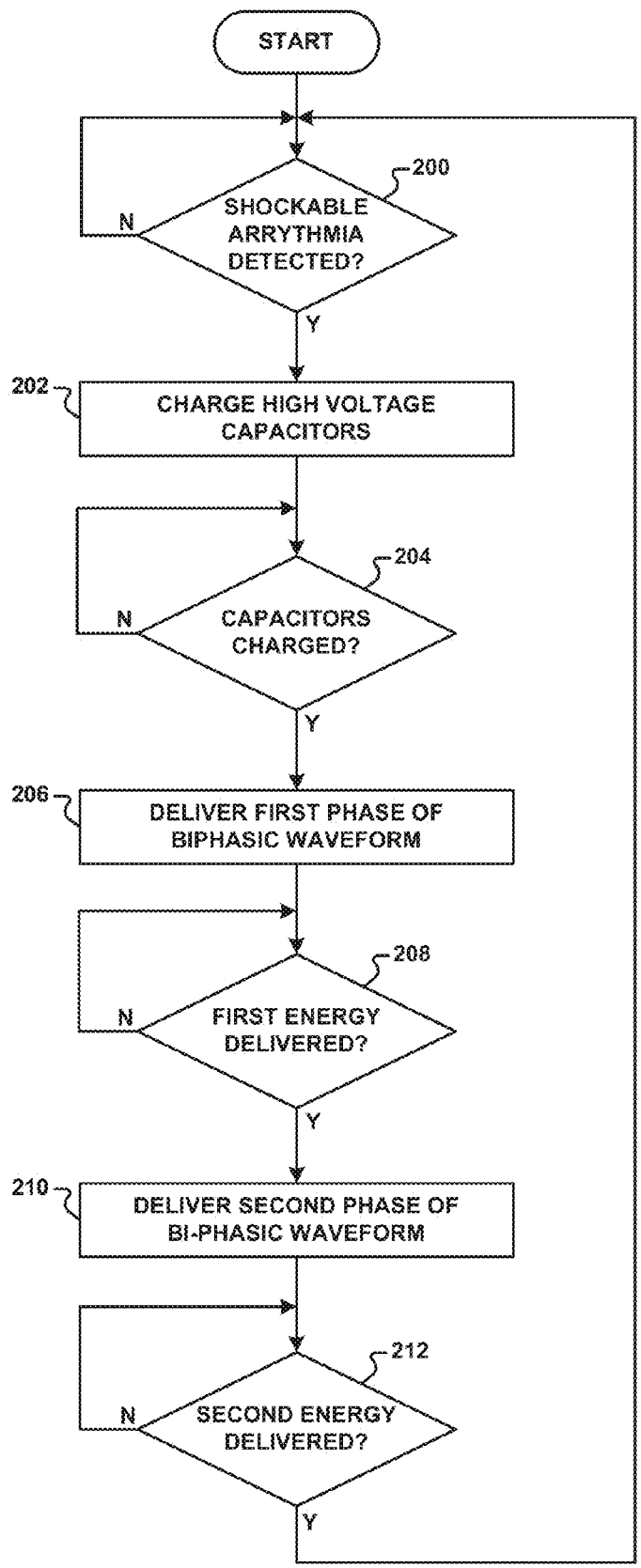
FIG. 9 is a flowchart of an example method for delivering high-energy therapy using a biphasic waveform.

FIG. 9 is a flowchart of a method for delivering high-energy therapy using a biphasic waveform. At the start of the method of FIG. 9, it may be assumed that processing module 132 is configured to deliver high-energy therapy using a biphasic waveform. The method of FIG. 9 describes a scenario where IMD 106 delivers a biphasic waveform without detecting a short circuit fault.

At the start of the method of FIG. 9, processing module 132 may be continuously monitoring heart rate to determine whether heart 102 is experiencing a shockable arrhythmia (200). If processing module 132 does not detect a shockable arrhythmia (e.g., VT/VF), processing module 132 continues monitoring heart rate. If processing module 132 detects a shockable arrhythmia, processing module 132 instructs charging module 152 to charge high-voltage capacitors 150 (202). Processing module 132 may monitor the voltage across high-voltage capacitors 150 during charging and determine whether high-voltage capacitors 150 are charged based on the magnitude of the monitored voltage (204). If processing module 132 determines that high-voltage capacitors 150 are not charged up to the charging voltage $V_0$, processing module 132 continues monitoring the voltage across high-voltage capacitors 150 until the appropriate threshold is reached.

If processing module 132 determines that high-voltage capacitors 150 are charged up to the charging voltage $V_0$, processing module 132 may disconnect charging module 152 from high-voltage capacitors 150 and control switching circuit 154 in order to deliver first phase 166 of a biphasic waveform (206). Processing module 132 may then monitor the voltage across high-voltage capacitors 150 in order to determine whether the first portion of energy has been delivered (208). If processing module 132 determines that the voltage across high-voltage capacitors 150 is greater than the first threshold voltage $V_{T1}$, processing module 132 may determine that the first portion of energy has not been delivered in block (208), and processing module 132 may continue to monitor the voltage across high-voltage capacitors 150.

If processing module 132 determines that the voltage across high-voltage capacitors 150 is less than or equal to $V_{T1}$, processing module 132 may determine that the first portion of energy has been delivered in block (208). Processing module 132 may then discontinue delivery of first phase 166 of the biphasic waveform, wait for a transition period, and then configure switching circuit 154 to deliver second phase 168 of the biphasic waveform (210).

Processing module 132 may then monitor the voltage across high-voltage capacitors 150 in order to determine whether the second portion of energy has been delivered (212). If processing module 132 determines that the voltage across high-voltage capacitors 150 is greater than the second threshold voltage $V_{T2}$, processing module 132 may determine that the second portion of energy has not been delivered in block (212), and processing module 132 may continue to monitor the voltage across high-voltage capacitors 150.

If processing module 132 determines that the voltage across high-voltage capacitors 150 is less than or equal to $V_{T2}$, processing module 132 may determine that the second portion of energy has been delivered in block (212). Processing module 132 may then discontinue delivery of second phase 168 of the biphasic waveform and return to monitoring the heart rate and determining whether a shockable arrhythmia is detected (200).

IMD 106 of the present disclosure may detect potential faults in components of IMD 106. For example, as described hereinafter, processing module 132 may detect potential faults based on information acquired during delivery of high-energy therapy. The potential faults may be manifested as short circuit faults in the electrical pathway from high-voltage capacitors 150 to electrodes 124, 127. When components of IMD 106 are functional, i.e., do not include short circuit faults, a continuous electrical pathway is present from high-voltage capacitors 150 to heart 102 through which high-energy therapy is delivered to heart 102. However, when the electrical pathway from high-voltage capacitors 150 to electrodes 124, 127 includes a short circuit fault, current may be redirected (e.g., shunted) such that the current is not delivered effectively to heart 102, but instead directed through the short circuit fault of the electrical pathway.

The electrical pathway from high-voltage capacitors 150 to electrodes 124, 127 during delivery of high-energy therapy may include a variety of components. For example, as illustrated, the electrical path may include some of switches 158, conductors in lead 114, and electrodes 124, 127. Additionally, the electrical pathway may include electrical connections within IMD 106 that connect high-voltage capacitors 150 to switches 158, the electrical connections that form interconnects between switches 158, and the electrical connections that connect conductors of lead 114 to electrical switches 158. The electrical interconnects between high-voltage capacitors 150 and switches 158 may include metallic traces on printed circuit boards (PCBs) that provide support for electrical components within IMD 106 and metallic wires that may be used to connect conductors in lead 114 to the PCB of IMD 106.

When components of IMD 106 (e.g., switches 158, conductive interconnects, conductors in lead 114, and electrodes 124, 127) are functional, high-voltage capacitors 150 may be connected to heart 102 during high-energy therapy such that the energy discharged from high-voltage capacitors 150 is delivered to heart 102. However, in some examples, components of IMD 106 that form the electrical path from high-voltage capacitors 150 to heart 102 may malfunction and produce a short circuit fault in the electrical path. The short circuit fault in the electrical path may be a low impedance path (e.g., approximately a short circuit) that redirects current away from heart 102. In other words, current conducted through a short circuit fault may not be delivered to heart 102, but instead may be dissipated in other areas of IMD 106. The redirection of current away from heart 102 may decrease the amount of energy delivered to heart 102 during high-energy therapy, and therefore may cause the attempted delivery of the high-energy therapy to be ineffective.

As described above, switches 158 typically present a high impedance when operating in the open state (e.g., an open circuit). A short circuit fault in a switch may cause a decrease in the impedance of the switch when the switch is instructed to operate in the open state by processing module 132. For example, when switches 158 are MOSFETs, a short circuit fault may include a fault that presents a decreased impedance from drain to source of the MOSFET when the MOSFET is intended to operate as an open switch. A short circuit fault in a switch may not necessarily be a near zero impedance, but instead, the short circuit fault in the switch may have an impedance value in between a zero impedance and an open circuit impedance that may allow current to flow through the switch in a manner that was not intended.

Typically, lead 114 includes separate conductors that extend from connector block 110 to electrodes 127. Conductors within lead 114 may typically provide separate low impedance paths from high-voltage capacitors 150 to heart 102. However, a short circuit fault may occur between the conductors of lead 114. A short circuit fault between the conductors may present a low impedance path (e.g., a short circuit) for current delivered from high-voltage capacitors 150 during delivery of high-energy therapy. A short between conductors of leads 114 may be either an intermittent or continuous short.

Typically, interconnections between electronic components of IMD 106 provide separate low impedance paths for current delivered from high-voltage capacitors 150. Interconnections, as used herein, may generally describe the conductive paths between components of IMD 106. For example, interconnects may include the conductive traces (e.g., on a PCB) and wires that connect high-voltage capacitors 150 to switches 158. Additionally, interconnects may also include the conductive traces and wires that connect switches 158 to conductors of lead 114. In some examples, short circuit faults may be present between interconnects. Short circuit faults between the interconnects may present a low impedance path for current delivered from high-voltage capacitors 150 during deliver of high-energy therapy. Such a short circuit fault between two interconnects may conduct current delivered from high-voltage capacitors 150 such that the current is redirected away from heart 102. A short circuit fault between two interconnects may be caused, for example, by fatigue and insulation breaches.

Additionally, interconnects may include the conductors of connector block 110. As described above, conductors in lead 114 may be mechanically connected to connector block 110 by screws, for example. When lead 114 is mechanically connected, conductors of lead 114 may be seated against conductive contacts within connector block 110 such that conductors of lead 114 are electrically connected to electrical components (e.g., switches 158) within IMD 106. In some examples, short circuit faults may be present in connector block 110, e.g., between electrical contacts of connector block 110 that may cause current from high-voltage capacitors 150 to be shunted away from heart 102. A short circuit fault in connector block 110 may include leakage paths between conductors, which may be caused by high voltage induced breakdown of insulating materials. In some examples, leakage paths may be present between conductors in the same bore (e.g., in a DF-4 or IS-4 connector standard), or between conductors in different bores, or between pathways that exit one bore and couple to another bore through conductive body fluids.

FIGS. 10-16 are schematics that illustrate example short circuit faults that may be present during delivery of high-energy therapy. It may be assumed that short circuits 175, 176, 177, 178 of FIGS. 10-16 present a low enough impedance to trigger detection of a short circuit fault by comparator module 155, and therefore are detectable by processing module 132. FIGS. 10-16 show a variety of different short circuit faults and potential switching configurations that may be used to work around such short circuit faults in order to provide high-energy therapy. Short circuits 175, 176, 177, 178 illustrated in FIGS. 10-16 may generally represent low impedance electrical connections that shunt current away from heart 102. Short circuits 175, 176, 177, 178 may be intermittent in nature, or continuous (i.e., permanent).

Figure 14:
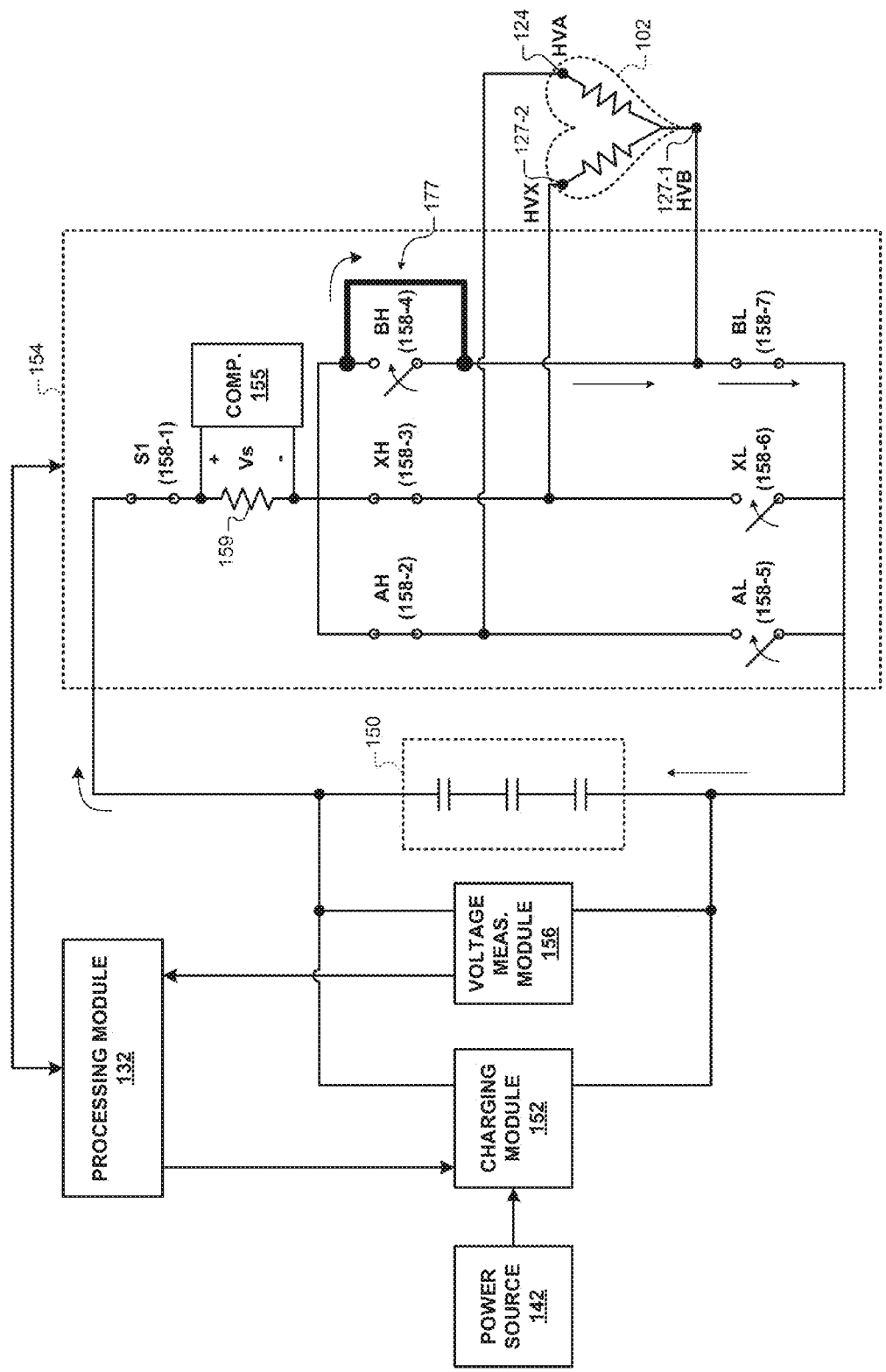
FIG. 14 is a schematic that illustrates an example short circuit fault in a switch of the IMD.

Detection of short circuit faults and potential switching configurations that may be used to bypass the short circuit faults are now described with respect to FIGS. 10-13. FIGS. 14-15 illustrate short circuit faults that may be present in switches 158. FIG. 16 illustrates using a shorted switch to deliver high-energy therapy. FIGS. 17-19 show methods for reconfiguring high-energy therapy in response to detection of a short circuit fault during delivery of high-energy therapy.

Figure 10:
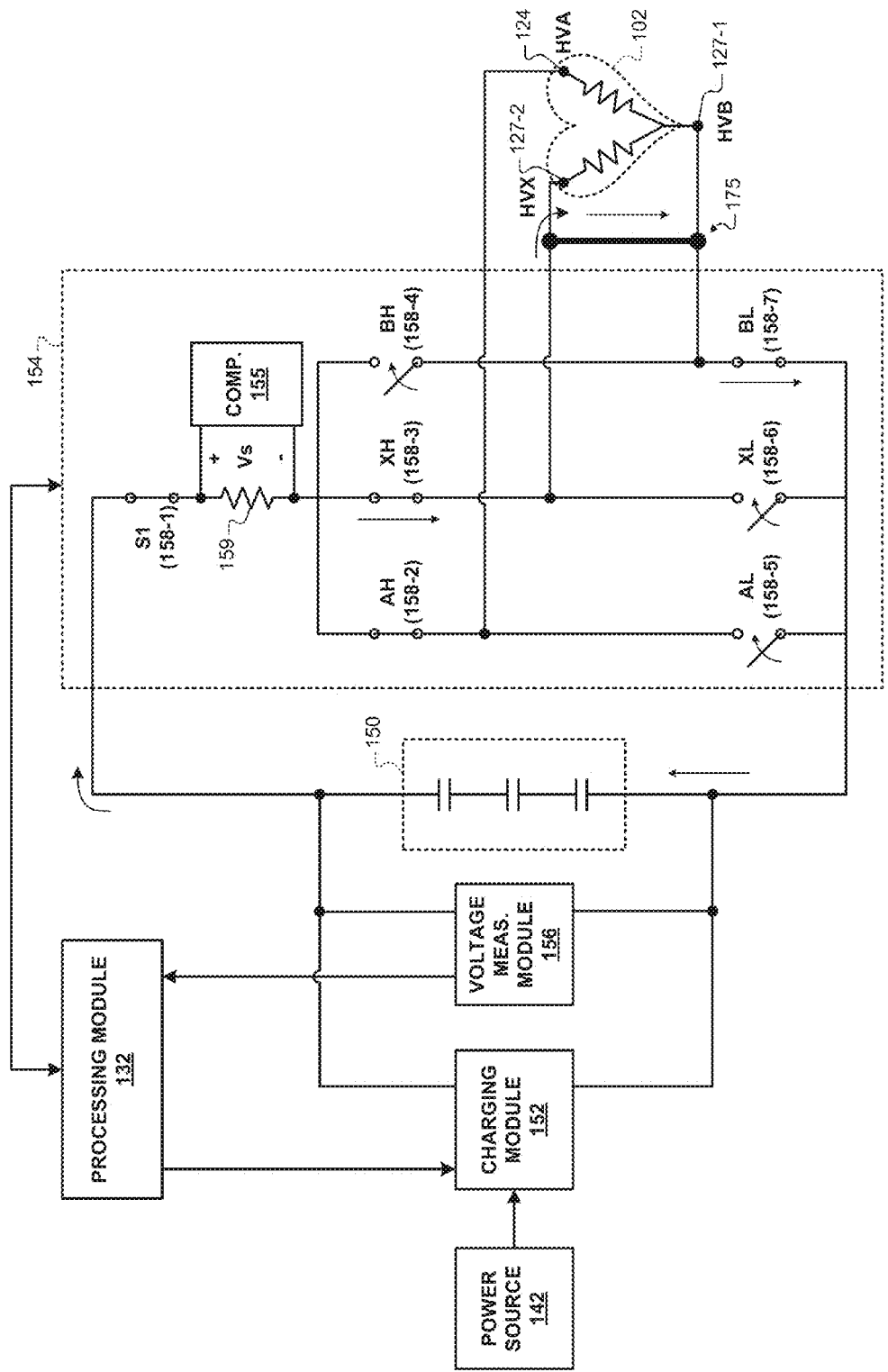
FIG. 10 is a schematic that illustrates an example short circuit fault that may be present during delivery of high-energy therapy.

FIG. 10 is a schematic that shows an example short circuit fault that may be present during delivery of high-energy therapy. The schematic may represent an attempted delivery of high-energy therapy during a first phase of a biphasic waveform using the AX>B vector. Short circuit 175 is illustrated between electrodes HVX 127-2 and HVB 127-1. Short circuit 175 may represent one or more types of faults. In one example, short circuit 175 may represent a short circuit in connector 110. In another example, short circuit 175 may represent a short circuit between conductors of lead 114.

Short circuit 175 may tend to direct current away from heart 102 during delivery of therapy. For example, short circuit 175 in parallel with heart 102, may tend to shunt current away from heart 102 during delivery of high-energy therapy. Short circuit 175 may generally represent a conductive path that may take on a range of impedances. The lower the impedance of short circuit 175, the more the current delivered by high-voltage capacitors 150 may be shunted away from heart 102 during delivery of high-energy therapy. The shunting of current away from heart 102 may cause an attempted therapy delivery to be ineffective.

Processing module 132 may detect a short circuit fault during delivery of high-energy therapy when short circuit 175 is present in the conductive pathway. During delivery of high-energy therapy according to the therapy configuration of FIG. 10, comparator module 155 may indicate that the amount of current through switching circuit 154 is greater than the threshold amount of current. Based on this indication from comparator module 155, processing module 132 may detect the short circuit fault.

Figure 11:
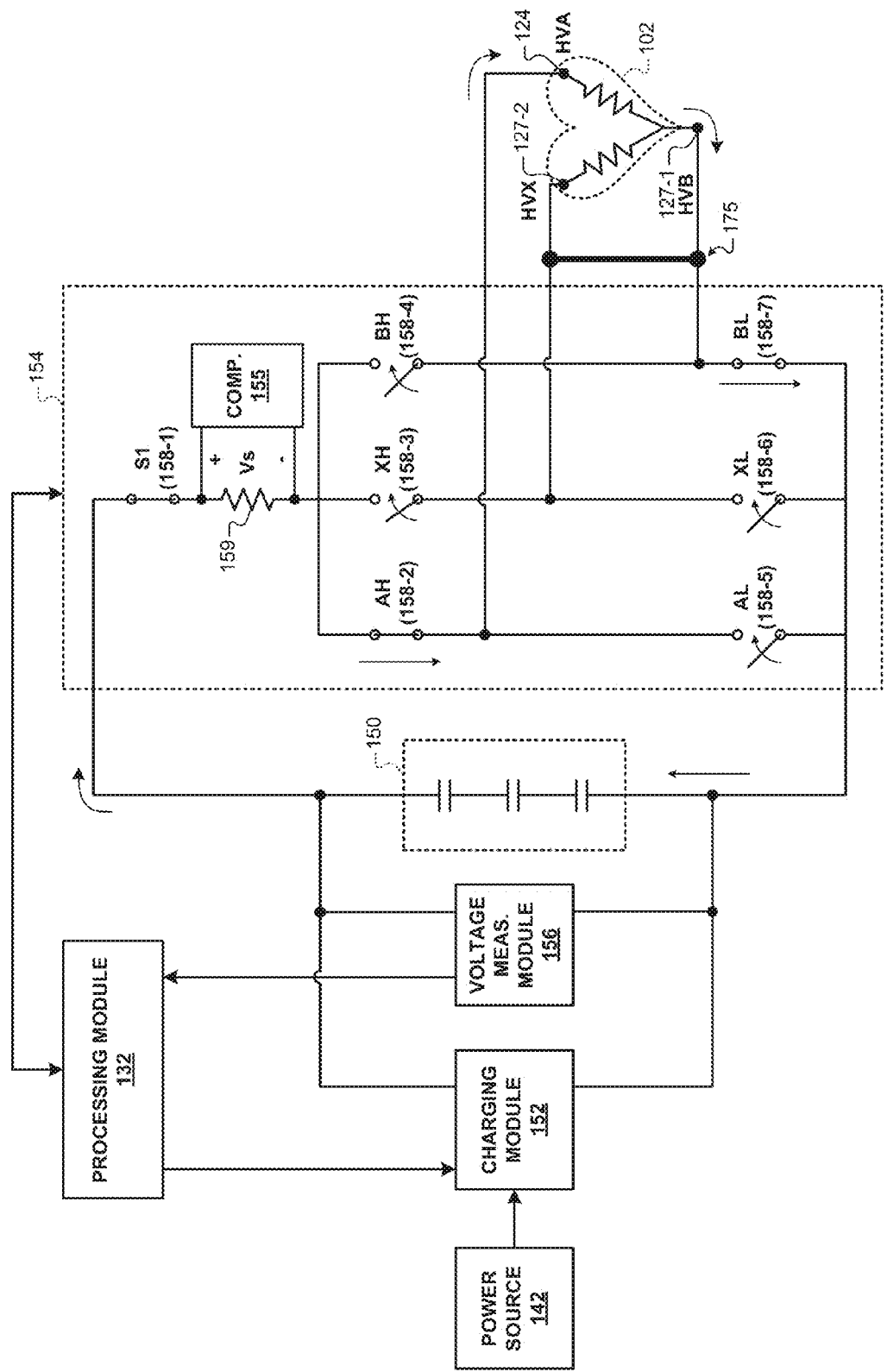
FIG. 11 is a schematic that illustrates an example switching configuration that may be used to bypass the short circuit fault of FIG. 10.

FIG. 11 shows a switching configuration of switching circuit 154 that may be used to work around the short circuit fault of FIG. 10. FIG. 11 illustrates that delivering high-energy therapy using electrode vector A>B may provide a work around of short circuit 175. According to FIG. 11, processing module 132 may deliver high-energy therapy using electrode vector A>B by closing switches AH 158-2 and BL 158-7. Using this switching configuration, current may be delivered to heart 102 via electrodes HVA 124 and HVB 127-1, bypassing short circuit 175 between HVX 127-2 and HVB 127-1.

Figure 12:
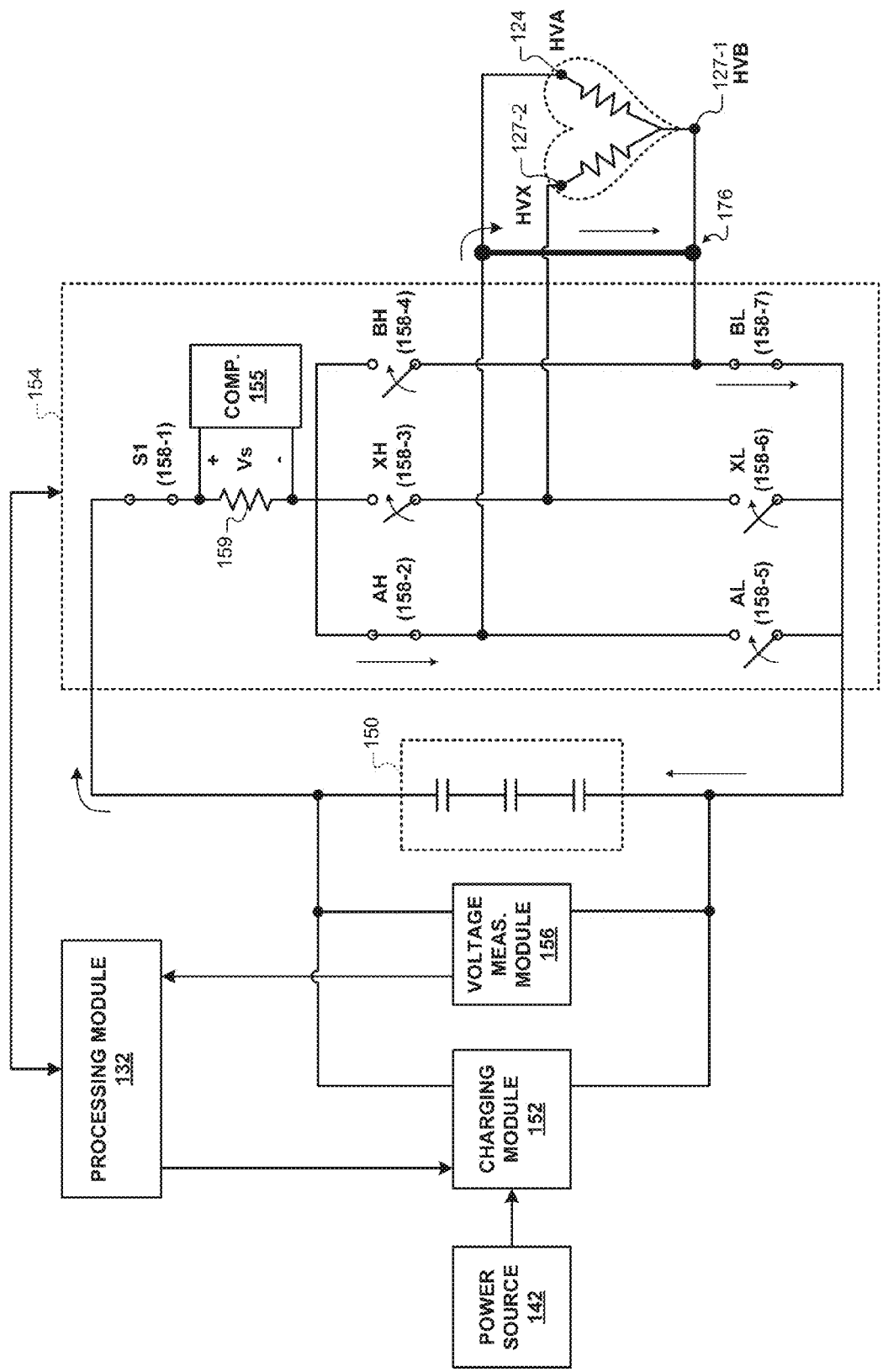
FIG. 12 is a schematic that illustrates another example short circuit fault that may be present during delivery of high-energy therapy.

FIG. 12 is a schematic that shows another example short circuit fault that may be present during delivery of high-energy therapy. Short circuit 176 is illustrated as a short circuit between electrodes HVA 124 and HVB 127-1. Short circuit 176 may represent one or more types of short circuit faults. In one example, short circuit 176 may represent a short circuit in connector 110. In another example, short circuit 176 may represent a short circuit between a conductor of lead 114 and HVA electrode 124, e.g., a short in the pocket between an exposed portion of lead 114 and HVA electrode 124. Short circuit 176 may tend to direct current away from heart 102 during delivery of therapy in a similar manner as short circuit 175 of FIG. 10. The shunting of current away from heart 102 through short circuit 176 may cause an attempted therapy delivery to be ineffective.

Processing module 132 may detect short circuit 176 of FIG. 12 in a similar manner as processing module 132 detects short circuit 175 of FIG. 10. For example, during delivery of high-energy therapy according to the therapy configuration of FIG. 12, processing module 132 may detect a short circuit fault based on an indication from comparator module 155 that the amount of current through switching circuit 154 is greater than the threshold amount of current.

Figure 13:
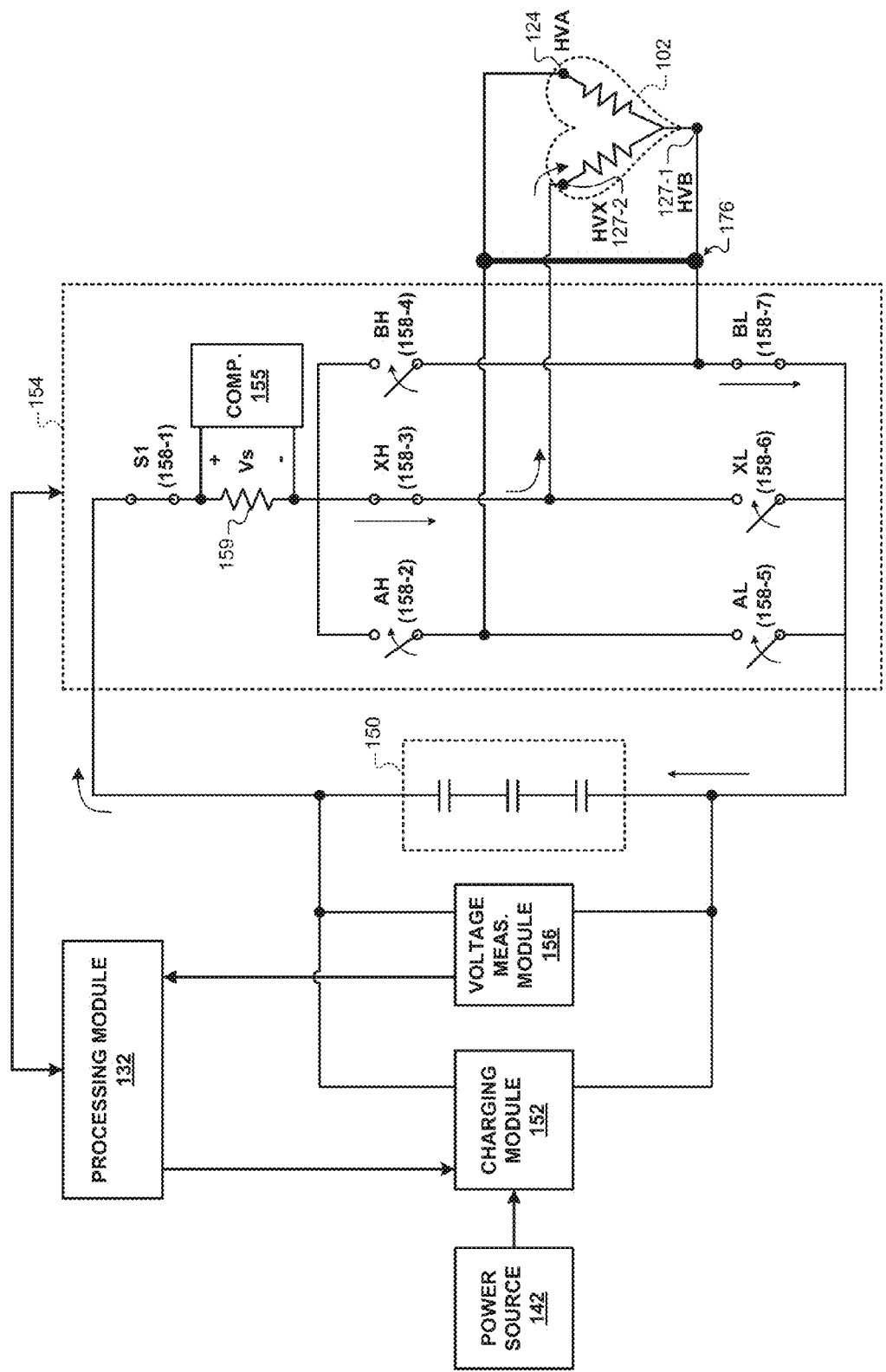
FIG. 13 is a schematic that illustrates an example switching configuration that may be used to bypass the short circuit fault of FIG. 12.

Note that although short circuit 175 of FIGS. 10-11 and short circuit 176 of FIGS. 12-13 are in different locations, short circuits 175, 176 may both be detected as short circuit faults that occur during delivery of high-energy therapy during a first phase of a biphasic waveform using the AX>B vector. In this respect, in some examples, processing module 132 may not differentiate between short circuit 175 and short circuit 176 based solely on detection of a short circuit fault during delivery of high-energy therapy during a first phase of a biphasic waveform using the AX>B vector. In some examples, IMD 106 may include additional short circuit fault detection components that may be used to distinguish between different types of short circuit faults.

However, processing module 132 may differentiate between short circuits 175, 176 based on the detection of subsequent short circuit faults, or the absence of short circuit faults, using different switching configurations. For example, even though processing module 132 may not differentiate between the short circuit faults caused by short circuits 175, 176 when using the AX>B vectors, processing module 132 may differentiate between detected short circuit faults when using the A>B vector. As described above with respect to FIG. 11, using electrode vector A>B may work around the short circuit fault caused by short circuit 175. However, as illustrated by FIG. 12, using electrode vector A>B to work around short circuit 176 may not be successful. Instead, processing module 132 may detect a short circuit fault when delivering high-energy therapy while using electrode vector A>B when short circuit 176 of FIG. 12 is present.

FIG. 13 shows a switching configuration of switching circuit 154 that may be used to bypass the short circuit fault of FIG. 12. FIG. 13 illustrates that delivering high-energy therapy using electrode vector X>B may provide a work around of short circuit 176. According to FIG. 13, processing module 132 may deliver high-energy therapy using electrode vector X>B by closing switches XH 158-3 and BL 158-7. Using this switching configuration, current may be delivered via electrodes HVX 127-2 and HVB 127-1, bypassing short circuit 176 between HVA 124 and HVB 127-1.

Although delivering high-energy therapy using electrode vector X>B may not be as efficacious as providing high-energy therapy using vector AX>B, in some examples, delivering therapy using vector X>B may be one of the few available vectors for therapy delivery, depending on the location of a detect short circuit fault. For example, as described above with respect to FIG. 12, processing module 132 may not deliver therapy using electrode vector AX>B due to short circuit 176, however, processing module 132 may be able to reconfigure the electrode vector in order to deliver high-energy therapy using electrode vector X>B. Although vector X>B may not provide a more efficacious therapy than other electrode vectors (e.g., AX>B), therapy via vector X>B may still successfully treat a shockable arrhythmia and return heart 102 to a normal rhythm, e.g., in cases where electrode X is an epicardial patch electrode on the myocardium. Accordingly, delivery of therapy via a less efficacious option (e.g., vector X>B) may prove effective in correcting an arrhythmia, and therefore may be more preferable than completely withholding high-energy therapy in response to detection of a short circuit fault.

FIG. 14 is a schematic that shows another example short circuit fault that may be present during delivery of high-energy therapy. Short circuit 177 is illustrated as a short circuit across switch BH 158-4. Short circuit 177 across switch 158-4 may present a low impedance path, regardless of whether processing module 132 has instructed switch 158-4 to open or close. Short circuit 177 may tend to direct current away from heart 102 and through switch BL 158-7 when switch BL 158-7 is closed during delivery of high-energy therapy. The shunting of current away from heart 102 through short circuit 177 may reduce the effectiveness of the delivered therapy.

Switching circuit 154, as illustrated in FIG. 14, is configured to deliver first phase 166 of a biphasic waveform using electrode vector AX>B. During delivery of first phase 166, processing module 132 may detect a short circuit fault based on an indication from comparator module 155 that the amount of current through switching circuit 154 is greater than the threshold amount of current.

Note that if short circuit 177 was not present in switch BH 158-4 in FIG. 14 during first phase 166, but instead present in switch BL 158-7 during first phase 166 of delivery using electrode vector AX>B, then the short circuit across switch BL 158-7 would not be detected during first phase 166. In other words, in some examples, processing module 132 may not detect a short circuit fault when a short circuit is present in a switch that processing module 132 has instructed to close. As described hereinafter with respect to FIG. 16, in some examples, a short circuit in a switch may be used for delivery of high-energy therapy.

FIG. 15 is a schematic that shows another example short circuit fault that may be present during delivery of high-energy therapy. Short circuit 178 is illustrated as a short circuit across switch BL 158-7. Short circuit 178 in switch BL 158-7 may present a low impedance path through switch BL 158-7, regardless of whether processing module 132 has instructed switch 158-7 to open or close. As described above, short circuit 178 in switch BL 158-7 may not be detected by processing module 132 during first phase 166 of delivery using electrode vector AX>B. However, short circuit 178 across switch BL 158-7 may be detected during second phase 168 of delivery using electrode vector AX>B.

Switching circuit 154, as illustrated in FIG. 15, is configured to deliver second phase 168 of a biphasic waveform using electrode vector AX>B. During delivery of second phase 168, processing module 132 may detect a short circuit fault based on an indication from comparator module 155 that the amount of current through switching circuit 154 is greater than the threshold amount of current. Short circuit 178 may tend to direct current away from heart 102 during second phase 168, which may reduce the effectiveness of the delivered therapy during second phase 168.

FIGS. 14-15 together illustrate that some short circuit faults may be detected during one phase of a biphasic waveform, but not during another phase of a biphasic waveform. For example, a short circuit in switch BH 158-4 may be detected during the first phase of a biphasic waveform, but not during a second phase of the biphasic waveform. Similarly, a short circuit in switch BL 158-7 may be detected during a second phase of a biphasic waveform, but not during the first phase of the biphasic waveform. Accordingly, the time when the short circuit fault is detected during delivery of high-energy therapy may provide information that indicates the location of the short circuit fault. The order in which new therapy configurations are selected by processing module 132 may be based on this information. In other words, processing module 132 may select a new therapy configuration based on the electrode vector that was being used when the short circuit fault was detected during the delivery of high-energy therapy and based on when (e.g., which phase) the short circuit fault was detected during delivery of the high-energy therapy.

With respect to FIGS. 10-16, note that in some examples, processing module 132 may not determine the exact location (e.g., conductor, or switch) of a short circuit after making only a single detection of a short circuit fault since there may be multiple causes of short circuit faults for a single therapy configuration. For example, with respect to FIGS. 10-13, shorts 175, 176, although in different locations, may both be detected as a short circuit fault during a first phase of a biphasic waveform using the AX>B vector.

Although processing module 132 may not specifically identify the location of a short circuit within the delivery pathway upon a single detection of a short circuit fault, processing module 132 may, in some examples, determine the location of a short circuit fault in IMD 106 with some degree of specificity after a sequence of short circuit faults are detected. For example, as described above, processing module 132 may detect shorts in switching circuit 154 based on the phase of delivery in which the short circuit fault was detected. In these examples, processing module 132 may select a therapy configuration from short circuit therapy configurations 162 that provides a delivery of therapy (e.g., monophasic) that compensates for the shorted switch by including the shorted switch in the delivery path. In other words, processing module 132 may, in some examples, determine that a short circuit is included in switching circuit 154 (e.g., in a switch), and subsequently select a therapy configuration that includes the short circuit in the delivery pathway. Thus, processing module 132 may intentionally, via selection of a therapy configuration, use a detected short circuit as a portion of the delivery pathway.

Referring now to FIG. 17, a flowchart illustrates a method for detecting short circuit faults during delivery of high-energy therapy using a biphasic waveform. It may be assumed that processing module 132 is configured to deliver high-energy therapy using a biphasic waveform, as illustrated in FIG. 5.

Processing module 132 may continuously monitor the heart rate of patient 104 and determine whether heart 102 is experiencing an arrhythmia (300). If processing module 132 does not detect a shockable arrhythmia, processing module 132 continues monitoring heart rate. If processing module 132 detects a shockable arrhythmia, processing module 132 instructs charging module 152 to charge high-voltage capacitors 150 to voltage $V_0$ (302).

Processing module 132 then instructs switching circuit 154 to deliver first phase 166 of a biphasic waveform (304). Processing module 132 may then monitor the current being delivered by high-voltage capacitors 150 during first phase 166. During first phase 166, processing module 132 may determine whether the amount of current being delivered by high-voltage capacitors 150 is greater than the threshold amount of current (306). If the amount of current being delivered by high-voltage capacitors 150 is greater than the threshold amount of current, then processing module 132 may detect a short circuit fault (308) and transition to delivering second phase 168 (310). If processing module 132 determines that the amount of current is not greater than the threshold amount of current, processing module 132 may determine whether the first amount of energy has been delivered (312). If the first portion of energy has not been delivered (i.e., Vcap>$V_{T1}$), then processing module 132 continues monitoring the current being delivered by high-voltage capacitors 150 in block (306). If processing module 132 determines that the first portion of energy has been delivered (i.e., Vcap≤$V_{T1}$) then processing module 132 may discontinue delivery of first phase 166 of the biphasic waveform, wait for a transition period, and then configure switching circuit 154 to deliver second phase 168 of the biphasic waveform (310).

Processing module 132 may then monitor the current being delivered by high-voltage capacitors 150 during second phase 168. During second phase 168, processing module 132 may determine whether the amount of current being delivered by high-voltage capacitors 150 is greater than the threshold amount of current (314). If the amount of current being delivered by high-voltage capacitors 150 is greater than the threshold amount of current, then processing module 132 may detect a short circuit fault (316) and end high-energy therapy delivery (318). If processing module 132 determines that the amount of current is not greater than the threshold amount of current, processing module 132 may determine whether the second amount of energy has been delivered (320). If processing module 132 determines that the second amount of energy has been delivered (i.e., Vcap≤$V_{T2}$) then processing module 132 may discontinue delivery of the high-energy therapy (318).

With respect to FIG. 3, as described above, memory 134 may include initial therapy configurations 160 and short circuit therapy configurations 162. Initially, before detection of a short circuit fault, processing module 132 may control the delivery of high-energy therapy using initial therapy configurations 160. For example, initial therapy configurations 160 may define a pattern of therapy configurations to be used by processing module 132 in scenarios where processing module 132 has not previously detected a short circuit fault during delivery of high-energy therapy.

Processing module 132 may control delivery of high-energy therapy according to initial therapy configurations 160 until a short circuit fault is detected during delivery of high-energy therapy, as described above. Upon detection of a short circuit fault during delivery of high-energy therapy, processing module 132 may begin delivering high-energy therapy according to short circuit therapy configurations 162 stored in memory 134. Short circuit therapy configurations 162 may represent N different therapy configurations 164. Each of the N therapy configurations 164 may define an electrode vector (e.g., AX>B, A>X, etc.), a waveform (e.g., biphasic/monophasic), and transition data. The transition data included in each of the N therapy configurations 164 may define a subsequent one of the N therapy configurations to select in response to detection of a short circuit fault at the current therapy selection. For example, the transition data may specify a subsequent one of the N therapy configurations to select based on when (e.g., during which phase of delivery) a short circuit fault was detected during delivery of high-energy therapy according to the current one of the N therapy configurations.

FIG. 18 shows a method for reconfiguring high-energy therapy based on detection of a short circuit fault during previous deliveries of high-energy therapy. At the start of the method of FIG. 18, it may be assumed that processing module 132 has not yet detected a short circuit fault during delivery of high-energy therapy. Accordingly, at the start of the method of FIG. 18, processing module 132 may select an initial therapy configuration (e.g., an initial electrode vector and waveform) for delivery of high-energy therapy from initial therapy configurations 160 (400). It may be assumed that the initial therapy configuration specifies that the waveform to be delivered during high-energy therapy is a biphasic waveform.

Processing module 132 may continuously monitor heart rate and determine whether heart 102 is experiencing a shockable arrhythmia (402). If processing module 132 does not detect a shockable arrhythmia, processing module 132 continues monitoring heart rate. If processing module 132 detects a shockable arrhythmia, processing module 132 instructs charging module 152 to charge high-voltage capacitors 150 and controls switching circuit 154 in order to deliver first phase 166 of a biphasic waveform (404). Processing module 132 may monitor the current delivered by high-voltage capacitors 150 during first phase 166.

Processing module 132 may determine whether a short circuit fault is present during first phase 166 (406). In examples where a short circuit fault is present during first phase 166, processing module 132 may detect the short circuit fault (408) and proceed to deliver second phase 168 of the biphasic waveform (410). In other examples, when processing module 132 does not detect a short circuit fault, processing module 132 may instruct switching circuit 154 to begin delivery of second phase 168 of the biphasic waveform after the first portion of energy is delivered. In some examples, processing module 132 may jump to block (418) upon detection of a fault in block 408.

Processing module 132 may monitor the current delivered by high-voltage capacitors 150 during second phase 168 to determine whether a short circuit fault is present during second phase 168 (412). In examples where a short circuit fault is present during second phase 168, processing module 132 may detect the short circuit fault (414). In other examples, when processing module 132 does not detect a short circuit fault, processing module 132 may instruct switching circuit 154 to stop delivery of second phase 168 of the biphasic waveform after the second portion of energy is delivered.

Processing module 132 may then determine whether a fault was detected during either the first or second phases 166, 168 of the biphasic waveform (416), e.g., in either block (408) or block (414). If processing module 132 did not detect a fault during delivery of the biphasic waveform, processing module 132 may continue monitoring the heart rate in order to detect shockable arrhythmias in block (402). If processing module 132 detected a short circuit fault during delivery of the biphasic waveform in either of blocks (408) or (414), processing module 132 may select a new therapy configuration to use during a subsequent delivery of high-energy therapy (418). In other words, processing module 132 may select a new therapy configuration (i.e., a new electrode vector and/or waveform) other than the initial configuration selected in block (400) and used to deliver the high-energy therapy during which the short circuit fault was detected in either block (408) or block (414). Processing module 132 may select the new therapy configuration from short circuit therapy configurations 162. For example, processing module 132 may identify the initial therapy configuration of block (400) in short circuit therapy configurations 162, then select the new therapy configuration based on the transition data associated with the initial therapy configuration of block (400). The transition data may indicate two different new therapy configurations for selection in block (418), e.g., a first new therapy configuration that should be selected if the short circuit fault was detected during first phase 166 at block (408), or a second new therapy configuration that should be selected if the short circuit fault was detected during second phase 168 at block (414). Processing module 132 may select one of the first and second new therapy configurations in block (418) based on when the fault was detected, e.g., based on the phase in which the fault was detected.

The first and second new therapy configurations, which may be selected in block (418), may be included in short circuit therapy configurations 162, and each of the first and second therapy configurations may also include transition data that indicates future selections of therapy configurations based on when faults are detected in the first and second therapy configurations. FIG. 20 is a state diagram that illustrates possible therapy configurations and selections of new therapy configurations based on when faults are detected.

With respect to FIG. 18, processing module 132 may then continue monitoring heart rate in order to determine whether a shockable arrhythmia is present (402). If a shockable arrhythmia is detected, processing module 132 may deliver high-energy therapy using the selected new therapy configuration, i.e., the new electrode vector and/or waveform selected in block (418).

FIG. 19 shows a method for selecting new therapy configurations in response to detection of short circuit faults. At the start of the method of FIG. 19, it may be assumed that processing module 132 is monitoring the heart rate of patient 104. Initially, processing module 132 is configured to deliver high-energy therapy according to an initial therapy configuration specified in initial therapy configurations 160 (500). The initial therapy configuration may specify an initial electrode vector and an initial waveform (e.g., either monophasic or biphasic).

Processing module 132 may monitor the heart rate of patient 104 to determine whether heart 102 is experiencing a shockable arrhythmia (502). If processing module 132 does not detect a shockable arrhythmia, processing module 132 continues to monitor the heart rate. If processing module 132 detects a shockable arrhythmia, processing module 132 instructs charging module 152 to charge high-voltage capacitors 150 and controls switching circuit 154 to deliver high-energy therapy according to the initial therapy configurations 160 (504), e.g., using the initial electrode vector and the initial waveform selected in block (500).

Processing module 132 may monitor the current delivered by high-voltage capacitors 150 during delivery of high-energy therapy according to the initial therapy configuration. Processing module 132 may determine whether a short circuit fault was present during delivery of high-energy therapy (506). If processing module 132 does not detect a short circuit fault, processing module 132 may continue to monitor the heart rate of patient 104 to determine whether a shockable arrhythmia is present in block (502).

If processing module 132 detected a short circuit fault during delivery of high energy therapy in block (504), processing module 132 may proceed to select a new delivery configuration from short circuit therapy configurations 162. As described above, short circuit therapy configurations 162 may specify N therapy configurations 164 that processing module 132 may use to deliver high-energy therapy. Each of N therapy configurations 164 may specify an electrode vector used for delivery of the high-energy therapy. Each of N delivery configurations 164 may also specify the type of waveform used for delivery of high-energy therapy. Each of N therapy configurations 164 may also include transitional data that specifies a subsequent therapy configuration of the N delivery configurations 164 that processing module 132 is to select in the event that a short circuit fault is detected during delivery using the current therapy configuration. When a current therapy configuration specifies that a biphasic waveform is to be delivered, the transitional data associated with that current therapy configuration may specify that processing module 132 is to select a first therapy configuration of the N therapy configurations 164 if a fault is detected during first phase 166, and that processing module 132 is to select a second therapy configuration of the N therapy configurations 164 if a fault is detected during second phase 168.

With respect to block (508), after a fault was detected during delivery of therapy according to the initial therapy configuration, processing module 132 may identify the initial therapy configuration in short circuit configurations 162 (508), then processing module 132 may select a new therapy configuration from short circuit configurations 162 based on when the fault was detected during delivery according to the initial therapy configuration (510). For example, processing module 132 may select the new therapy configuration from short circuit configurations 162 based on which phase of the biphasic waveform presented the short circuit fault. The new therapy configuration to be selected may be specified by transitional data associated with the initial therapy configuration.

Processing module 132 may then monitor the heart rate of patient 104 to determine whether patient 104 is experiencing a shockable arrhythmia (512). If processing module 132 does not detect a shockable arrhythmia, processing module 132 continues to monitor the heart rate (512). If processing module 132 detects a shockable arrhythmia, processing module 132 instructs charging module 152 to charge high-voltage capacitors 150 and controls switching circuit 154 to deliver high-energy therapy according to the new therapy configuration selected in block (510) from short circuit configurations 162 (514).

Processing module 132 may monitor the current delivered by high-voltage capacitors 150 during delivery of high-energy therapy according to the new therapy configuration. Processing module 132 may determine whether a short circuit fault was present during delivery of high-energy therapy (516). If processing module 132 does not detect a short circuit fault, processing module 132 may continue to monitor the heart rate of patient 104 to determine whether a shockable arrhythmia is present in block (512).

If processing module 132 detected a short circuit fault during delivery of high energy therapy in block (514), processing module 132 may proceed to select another new delivery configuration from short circuit therapy configurations 162 in block (508). For example, processing module 132 may select the next therapy configuration based on the current therapy configuration and based on when the fault was detected in block (514). Processing module 132 may select the next therapy configuration according to transition data associated with the current therapy configuration, as described above.

According to the method of FIG. 19, processing module 132 may continue to update the therapy configuration used to deliver high-energy therapy so long as short circuit faults continue to be detected during delivery of the high-energy therapy. In this manner, processing module 132 may selectively transition from one therapy configuration to another according to the pattern specified in short circuit configurations 162.

FIG. 20 shows a state diagram that graphically illustrates example short circuit therapy configurations 162 that may be selected by processing module 132. Each state of FIG. 20 indicates one of the N therapy configurations. For example, state 180-1 (i.e., configuration 180-1) represents a therapy configuration that specifies electrode vector AX>B and a biphasic waveform. As another example, state 180-2 represents a therapy configuration that specifies electrodes B>AX and a monophasic waveform. The transition conditions "PW1 Fault" and "PW2 Fault" may represent detection of a fault during first and second phases 166, 168, respectively. The transition labeled "Fault" may indicate that a fault was detected during monophasic pulse 172.

The transition "OK", that may redirect back to the same state, may indicate that no fault was detected during delivery of high-energy therapy and that processing module 132 may continue using the same therapy configuration in an event that no fault is detected. The transition "OK Eff." associated with state 180-3 may indicate that no fault was detected during delivery of high-energy therapy and that the therapy using therapy configuration 180-3 was effective in correcting the arrhythmia. The transition "OK Less Eff." associated with state 180-3 may indicate that no fault was detected during delivery of high-energy therapy but that the therapy delivered was not effective. Using a B>X vector in some systems may not be clinically effective in correcting arrhythmias, even if the energy was successfully delivered, however, some systems may have viable B>X pathways. The dotted lines may reflect transitions for systems that are implanted as two electrode systems that do not include an "X" electrode.

The states and the transitions between the states in FIG. 20 may illustrate example data included in short circuit configurations 162. For example, a state (e.g., 180-1) may indicate a current therapy configuration in short circuit configurations 162. The transitions from the state may represent data included in transition data that indicates a subsequent therapy configuration based on when a fault was detected in the current state. State 180-1, that specifies therapy configuration AX>B and a biphasic waveform, may transition to state 180-5 or state 180-6, depending on when a fault was detected. Transition data associated with configuration 180-1 may indicate that if a fault is detected during first phase ($PW_1$) 166 of therapy configuration 180-1, processing module 132 is to select therapy configuration 180-6 for subsequent deliveries of high-energy therapies. Transition data associated with configuration 180-1 may also indicate that if a fault is detected during second phase ($PW_2$) 168 of therapy configuration 180-1, processing module 132 is to select therapy configuration 180-5 for subsequent deliveries of high energy therapies.

According to FIG. 20, short circuit therapy configurations 162 may include therapy configurations using only two electrodes and therapy configurations using three electrodes. Therapy configurations using only 2 electrodes may use either monophasic or biphasic waveforms, and therapy configurations using three electrodes may use either monophasic or biphasic waveforms. In some examples, transition data may indicate that processing module 132 should transition from a therapy configuration using three electrodes to a therapy configuration using only two electrodes. For example, if processing module 132 detects a fault during delivery of therapy according to therapy configuration 180-1, which uses three electrodes, processing module 132 may select therapy configuration 180-6, which may include only 2 electrodes.

In some examples, transition data may indicate that processing module 132 transition from a therapy configuration using a biphasic waveform to a therapy configuration using a monophasic waveform. For example, if processing module 132 detects a fault during delivery of therapy according to therapy configuration 180-1, which uses a biphasic waveform, processing module 132 may select therapy configuration 180-5, which uses a monophasic waveform.

As described above, processing module 132 may transition from initial therapy configurations 160 to short circuit configurations 162 upon detection of a fault. Processing module 132 may perform the transition from initial therapy configurations 160 to short circuit configurations 162 by first determining the current therapy configuration (i.e., of initial therapy configurations 160) in which a fault was detected. Then, processing module 132 may identify that current therapy configuration in short circuit configurations 162. Then processing module 132 may determine the subsequent therapy configuration based on the transition data associated with the identified therapy configuration. In terms of the state diagram of FIG. 20, assuming processing module 132 controlled delivery of therapy using an initial therapy configuration of "AX>B, biphasic" from initial therapy configurations 160, and further assuming that processing module 132 detected a fault during first phase 166 using that configuration, processing module 132 would first identify therapy configuration 180-1 in short circuit configurations 162. Then processing module 132 would select therapy configuration 180-6 since the fault was detected during first phase 166 of the previously delivered therapy. Accordingly, processing module 132 would select a subsequent therapy configuration 180-6 (in short circuit configurations 162) in response to detecting a fault during first phase 166 of therapy configuration "AX>B, biphasic" included in initial therapy conditions 160.

Although a single state diagram is illustrated in the present disclosure, the state diagram of FIG. 20 should not be considered to be an exhaustive example of all state diagrams, nor should the state diagram of FIG. 20 be considered to be an exhaustive example of all possible short circuit configurations 162 (i.e., electrode vectors, waveforms, transitions). It is contemplated that other short circuit configurations may be implemented according to the present disclosure, e.g., different electrode vectors, waveforms, and transitions, depending on the components included in IMD 106, the arrangement of the electrodes of IMD 106, and the types of potential faults that may occur in IMD 106.

The electrode vectors and waveforms used in short circuit therapy configurations 162 along with the transitions between short circuit therapy configurations 162 may be created based on a variety of parameters and then subsequently programmed into IMD 106. For example, short circuit therapy configurations 162 may be created based on knowledge of the components included in IMD 106, knowledge of potential faults that may occur in IMD 106 (e.g., in switches 158, conductors in leads 112, 114, 116, and interconnects), and knowledge of the probability that such potential faults may occur. In other words, short circuit configurations 162 may be hardware specific parameters that are defined based on knowledge of the hardware included in IMD 106, and knowledge of the potential problems that may be caused by particular hardware failures in the device. Creation of short circuit therapy configurations 162 based on this knowledge of potential faults may allow for programming of improved therapy reconfiguration patterns into IMD 106. Such improved therapy reconfigurations may increase the probability of avoiding short circuit faults during subsequent therapy deliveries while simultaneously maintaining an efficacious therapy configuration for treatment of a detected arrhythmia.

FIG. 21 shows a table that includes information that may be used to generate a pattern of therapy configurations for delivery of defibrillation therapy in response to detection of short circuit faults. In other words, the table of FIG. 21 may include information that may be used to generate short circuit configurations 162. The information included in the table may be based on the components and operation of IMD 106 as described herein with respect to FIG. 4. In other words, the information included in FIG. 21 may be based on knowledge of the layout of switches 158 and the connections between switches 158 and electrodes 124, 127 during delivery of high-energy therapy using either monophasic, biphasic, or multiphasic waveforms.

FIG. 21 shows a table that lists potential reconfiguration options in response to detection of short circuit faults. The first column lists electrode vectors and waveforms that may be used to delivery high-energy therapy. The second column lists potential short circuit faults that may occur when delivery is attempted using the therapy configurations of the first column. The third column lists the possible causes of short circuit faults as detected according to the second column. The fourth column lists the subsequent therapy configurations that may be attempted in order to bypass the short circuit fault according to the second column.

As illustrated in FIG. 21, faults detected in therapy configurations may be associated with the components of the IMD, e.g., the switches, conductors in leads, and electrodes. Based on the possible causes of the short circuit faults, as described in FIG. 21, short circuit therapy configurations may be generated that may work around detected short circuit faults. Such short circuit therapy configurations, which may be based on the specific hardware configuration of IMD 106, may provide a robust fault tolerant therapy selection pattern for IMD 106.

The state diagram of FIG. 20 and the table of FIG. 21 may have been constructed by taking into account two different considerations. First, the potential reconfiguration vectors may have been selected in order to attempt to avoid failures detected during prior therapy configurations. Second, although avoidance of prior failures is a concern, the potential reconfiguration vectors may also be based on the suspected efficacy of a potential reconfiguration. Accordingly, short circuit configurations 162 may be generated by selecting those therapy configurations that are most efficacious while at the same time having a high probability of working around detected faults. In some examples, the probability and efficacy determinations, and accordingly, the generation of short circuit configurations 162, may be based on clinically observed data.

In some examples, after implantation in patient 104, processing module 132 may store, in memory 134, information relating to detected faults. For example, processing module 132 may store the pattern of therapy configurations attempted in response to detected faults along with the timing of the detected faults. In some examples, the clinician may retrieve the information relating to detected faults from IMD 106 via programmer 130 and use the information to diagnose potential problems with IMD 106.

As described above, the IMD of the present disclosure may step through a variety of different therapy configurations in order to bypass one or more detected short circuit faults. Although the IMD of the present disclosure is described above as stepping through a variety of different therapy configurations in response to detection of short circuit faults, the IMD of the present disclosure may use similar techniques as described herein to step through a variety of different therapy configurations in response to detection of high impedance faults that increase the impedance of the pathway as seen by the energy storage device during delivery of high-energy therapy. For example, the IMD of the present disclosure may select a subsequent therapy configuration based on the parameters of the current therapy configuration (e.g., the electrode vector and waveform) and based on when the high impedance fault occurred during delivery according to the current therapy configuration (e.g., during either the first or second phase of a biphasic waveform). In this manner, the IMD of the present disclosure may step through a variety of different therapy configurations in order to bypass one or more detected high impedance faults. Example techniques for stepping through a variety of different therapy configurations in order to bypass one or more detected high impedance faults is described in U.S. patent application Ser. No. 13/221,558, filed herewith, and entitled "Fault-Tolerant High Voltage Delivery in an Implantable Medical Device", which is incorporated herein by reference in its entirety.

Various examples have been described. These and other examples are within the scope of the following claims.

What is claimed is:

1. An implantable medical device comprising:
   an energy storage device configured to store electrical energy for delivery of a defibrillation therapy to a heart;
   a plurality of electrodes;
   a switching circuit configured to connect the plurality of electrodes to the energy storage device;
   a memory storing a plurality of initial therapy configurations and transition data associated with each one of the plurality of initial therapy configurations, the transition data comprising a second therapy configuration and a third therapy configuration for each one of the plurality of initial therapy configurations, each of the plurality of initial therapy configurations and the associated second and third therapy configurations individually defining a set of the plurality of electrodes and a waveform for delivering the defibrillation therapy; and
   a processing module configured to:
      control the switching circuit to deliver the defibrillation therapy using a first one of the initial therapy configurations comprising a first set of the plurality of electrodes and using a biphasic waveform that includes first and second phases;
      detect a short circuit fault during the biphasic waveform;
      determine which one of the first phase and the second phase of the biphasic waveform the short circuit fault is detected in; and
      responsive to detecting the short circuit fault during the first one of the initial therapy configurations, select one of the second therapy configuration and the third therapy configuration according to the transition data associated with the first one of the initial therapy configurations for delivery of a subsequent defibrillation therapy,
      the second therapy configuration being selected if the short circuit fault is detected during the first phase,
      the third therapy configuration being selected if the short circuit fault is detected during the second phase,
      the second therapy configuration being different than the first one of the initial therapy configurations and comprising a second set of the plurality of electrodes and one of a biphasic or monophasic waveform.

2. The medical device of claim 1, further comprising conductors coupling the plurality of electrodes to the switching circuit, and wherein the short circuit fault includes a short circuit between the conductors.

3. The medical device of claim 1, wherein the short circuit fault includes a short circuit between at least two of the plurality of electrodes.

4. The medical device of claim 1, further comprising conductors coupling the plurality of electrodes to the switching circuit, and wherein the short circuit fault includes a short circuit between one of the conductors and one of the plurality of electrodes.

5. The medical device of claim 1, wherein the switching circuit includes a plurality of switches, wherein the processing module is configured to instruct one of the plurality of switches to remain open during delivery of defibrillation therapy using the first set of the plurality of electrodes, and wherein the short circuit fault includes a malfunction in the one of the plurality of switches that causes the one of the plurality of switches to present a short circuit impedance when instructed to remain open.

6. The medical device of claim 1, wherein the processing module is configured to control the switching circuit to deliver defibrillation therapy according to the second set of the plurality of electrodes and the selected one of the biphasic or monophasic waveforms.

7. The medical device of claim 1, wherein the second set of the plurality of electrodes is the same as the first set of the plurality of electrodes.

8. The medical device of claim 1, wherein the first set of the plurality of electrodes includes three electrodes, and wherein the second set of the plurality of electrodes includes only two electrodes.

9. The medical device of claim 1, wherein the first set of the plurality of electrodes includes only two electrodes, and wherein the second set of the plurality of electrodes includes three electrodes.

10. The medical device of claim 1, wherein the first set of the plurality of electrodes includes three electrodes, and wherein the second set of the plurality of electrodes includes three electrodes.

11. The medical device of claim 1, wherein the fault is a short circuit path that shunts current away from the heart during delivery of defibrillation therapy.

12. The medical device of claim 1, wherein the third therapy configuration is different than the first one of the initial therapy configurations and the second therapy configuration associated with the first one of the initial therapy configurations.

13. The medical device of claim 1, wherein the memory further comprises transition data defining a next therapy configuration for each of the second therapy configuration and the third therapy configuration associated with each of the plurality of initial therapy configurations;
   the processor configured to:
      detect a short circuit fault during the subsequent defibrillation therapy delivery using the selected one of the second therapy configuration and the third therapy configuration associated with the first one of the initial therapy configurations, and
      responsive to detecting the short circuit fault during the subsequent defibrillation therapy, select the next therapy configuration for the respective one of the second therapy configuration and the third therapy configuration according to the stored transition data for delivery of a next subsequent defibrillation therapy.

14. The medical device of claim 1, wherein the processor is further configured to:
   control the switching circuit to deliver the defibrillation therapy using a second one of the initial therapy configurations if the first one of the initial therapy configurations is not successful in defibrillating the heart and a short circuit fault is not detected during the biphasic waveform of the first one of the initial therapy configurations, the second one of the initial therapy configurations comprising a different set of the plurality of electrodes than the first set of electrodes and a biphasic waveform;
   detect a short circuit fault during the biphasic waveform of the second one of the initial therapy configurations; and responsive to detecting the short circuit fault during the second one of the initial therapy configurations, select one of a second therapy configuration and a third therapy configuration according to the transition data associated with the second one of the initial therapy configurations for delivery of a subsequent defibrillation therapy.

* * * * *